United States Patent
Keller

(10) Patent No.: US 12,239,950 B2
(45) Date of Patent: Mar. 4, 2025

(54) PROCESS AND APPARATUS FOR SEQUENTIAL SYNTHESIS OF BIOLOGICAL POLYMERS

(71) Applicant: NITTO DENKO AVECIA INC., Milford, MA (US)

(72) Inventor: Karsten Keller, Mendon, MA (US)

(73) Assignee: Nitto Denko Avecia, Inc., Milford, MA (US)

( * ) Notice: Subject to any disclaimer, the term of this patent is extended or adjusted under 35 U.S.C. 154(b) by 726 days.

(21) Appl. No.: 17/442,015

(22) PCT Filed: Apr. 9, 2020

(86) PCT No.: PCT/US2020/027445
§ 371 (c)(1),
(2) Date: Sep. 22, 2021

(87) PCT Pub. No.: WO2020/210476
PCT Pub. Date: Oct. 15, 2020

(65) Prior Publication Data
US 2022/0176334 A1  Jun. 9, 2022

Related U.S. Application Data

(60) Provisional application No. 62/831,853, filed on Apr. 10, 2019.

(51) Int. Cl.
*B01J 19/00*   (2006.01)
*C07H 21/00*   (2006.01)

(52) U.S. Cl.
CPC .......... *B01J 19/0046* (2013.01); *C07H 21/00* (2013.01); *B01J 2219/00328* (2013.01);
(Continued)

(58) Field of Classification Search
CPC .......... B01J 19/0046; B01J 2219/00328; B01J 2219/00452; B01J 2219/00585;
(Continued)

(56) References Cited

U.S. PATENT DOCUMENTS

2002/0045221 A1   4/2002 Dellinger et al.
2002/0120128 A1   8/2002 Stockl
(Continued)

FOREIGN PATENT DOCUMENTS

DE    10347311 A1    5/2005
WO    1992021079 A1   11/1992
(Continued)

OTHER PUBLICATIONS

International Search Report for PCT/US2020/027445, Mailed Aug. 3, 2020, 4 pages.
(Continued)

*Primary Examiner* — Lessanework Seifu
(74) *Attorney, Agent, or Firm* — Lippes Mathias LLP

(57) ABSTRACT

A method and apparatus for nucleic acid synthesis. The method employs a device including at least one deprotection unit to carry out a step of deprotection, at least one coupling unit to carry out a step of coupling, at least one oxidation/thiolation unit to carry out a step of oxidation or thiolation, at least one capping unit to carry out a step of capping, and at least one washing unit to carry out a step of washing. A plurality of reaction vessels for nucleic acid synthesis are moved to the units in accord with a synthesis scheme for a desired nucleic acid sequence and at least two reaction vessels are simultaneously acted upon at several of the units in series.

19 Claims, 25 Drawing Sheets

STAGE 1 - STEP 4

(52) U.S. Cl.
CPC .............. *B01J 2219/00452* (2013.01); *B01J 2219/00585* (2013.01); *B01J 2219/0059* (2013.01); *B01J 2219/00722* (2013.01); *B01J 2219/00725* (2013.01)

(58) Field of Classification Search
CPC ...... B01J 2219/0059; B01J 2219/00722; B01J 2219/00725; B01J 2219/00283; B01J 2219/00599; B01J 2219/00711; B01J 2219/0072; B01J 2219/00729; C07H 21/00; C07K 1/045
See application file for complete search history.

(56) References Cited

U.S. PATENT DOCUMENTS

2005/0169816 A1    8/2005  Kirshner
2020/0063173 A1*  2/2020  Buersgens .............. C12P 19/34

FOREIGN PATENT DOCUMENTS

| | | |
|---|---|---|
| WO | 2004039953 A2 | 5/2004 |
| WO | 2005115102 A2 | 12/2005 |
| WO | 2007033176 A2 | 3/2007 |
| WO | 2019002237 A1 | 1/2019 |

OTHER PUBLICATIONS

European Search Report for Application No. 20788327.3, dated Dec. 12, 2022, 7 pages.

\* cited by examiner

STAGE 1 - STEP 1

STAGE 1 - STEP 4

STAGE 1 - STEP 4

STAGE 1 - STEP 4

STAGE 1 - STEP 4

STAGE 1 - STEP 6

STAGE 1 - STEP 8

PROCESS AND APPARATUS FOR SEQUENTIAL SYNTHESIS OF BIOLOGICAL POLYMERS

This application claims the benefit of U.S. Provisional Application 62/831,853, filed Apr. 10, 2019, the disclosure of which is herein incorporated by reference.

BACKGROUND

The present exemplary embodiment relates to systems and methods for synthesizing molecules. More specifically, the present embodiments relate to devices and methods for synthesizing biological polymers such as polypeptides and oligonucleotides. However, it is to be appreciated that the present exemplary embodiment is also amenable to other similar applications.

An oligonucleotide is a macromolecule comprising a sequence of nucleosides, each of which includes a sugar and a nucleobase. Each nucleoside is separated from adjacent nucleosides with an internucleosidic linkage, which effectively serves to bond the nucleosides together. The sugar can be a pentose, such as a deoxyribose, ribose, or 2'-O-substituted ribose. A number of different bases and substituted bases can be used, the four most common of which are adenine, cytosine, guanine, and thymine (abbreviated as A, C, G, and T, respectively). The internucleosidic linkage is most commonly a phosphate, which may be substituted with a variety of substituents at a nonbridging oxygen atom, most commonly by sulphur or an alkyl, ester, or amide group.

Oligonucleotides are among the most important and prevalent reagents used in biotechnology laboratories engaged in research, diagnostics and therapeutics. The high demand for oligonucleotides derives from their specificity for complementary nucleotide sequences in DNA or RNA obtained from biological samples. Different methods are used for synthesizing oligonucleotides, including phosphoramidite, phosphotriester, and H-phosphonate methods, each of which is generally known in the field of biochemistry.

Solid-phase based, multi-stage synthesis of complex organic molecules using controlled fluid flow across a fixed bed is one accepted methodology of nucleic acid synthesis. This general technique has been successfully applied to the synthesis of peptides, oligonucleotides and similar long-chained biological polymers. A comprehensive discussion of the chemistry and synthesis techniques for oligonucleotide production appears in "Manufacturing of Oligonucleotides", E. Paredes, V. Aduha, KL. Ackley, and H. Cramer, Comprehensive Medical Chemistry, $3^{rd}$ Edition, 2017 Elsevier Inc., herein incorporated by reference.

Commercial-scale production of a growing variety of oligonucleotides has become increasingly important as these substances have moved out of the laboratory and into mainstream therapeutic applications. Commercially available oligonucleotides are typically at least 6 nucleotides in length, sometimes 12-50 nucleotides long, with 15 to 30 nucleotides being the most common length.

In one system for producing oligonucleotide molecules, a solid support can be provided in a reaction vessel and a large number of dimethoxytrityl (DMT)-protected nucleosides can be fixed to the solid support. A deprotectant, acting through a detritylation mechanism, is added to remove the DMT from the nucleoside, and thus to "deprotect" the hydroxyl. As a result, the last nucleoside in the sequence has one hydroxyl that is ready to receive a next amidite. Nucleoside phosphoramidites (hereafter also referred to as "amidites"), dissolved in a solvent such as acetonitrile (ACN), are introduced into the vessel. An activator can also be introduced into the vessel with the amidites. The phosphorus in the amidites bonds with the oxygen in the hydroxyl, thus providing support-bound nucleotides. After the support-bound nucleotides are formed, excess amidites can be flushed from the vessel with ACN. An oxidizing agent can then be added to convert the trivalent phosphorous to pentavalent. After the oxidizing agent is flushed, a capping agent can be added to block the unprotected hydroxyls from reacting with amidites introduced at a later stage. ACN can again be introduced to flush out the capping agent. These steps can be repeated a number of times to produce growing oligonucleotide chains from support-bound nucleosides.

Traditional synthesizers use a flow-through design in which various lines, pumps, and valves are constantly filled with liquid and the liquid is introduced into a vessel (called a "column"). Columns are typically flow-through devices wherein a newly introduced liquid displaces a previously introduced liquid. Often, large manufacturing facilities achieve high throughput by employing an array of synthesizers in a batch process. These synthesizers are typically configured to perform individual steps of the monomer addition cycle in succession, and can do so for several different oligonucleotides in parallel. Thus, the sequence of reactions for a plurality of oligonucleotides is performed in order such that detritylation is carried out for each oligonucleotide, then coupling is carried out for each oligonucleotide, followed by capping of each oligonucleotide followed by oxidation of each oligonucleotide. The cycle is then repeated until full length oligonucleotides are obtained.

To manufacture biological polymers (e.g. oligonucleotides, peptides or others) at large scale, a widely accepted solid phase synthesis approach can be used. In this approach, a starting monomer is attached via a labile linker to an insoluble matrix. To this matrix, requisite regents and additional reactive monomers are added to grow the oligomeric compound onto the insoluble bead. Specifically, the solid-phase synthesis cycle for the manufacture of oligonucleotides can be generally performed in four iterative steps. Initially, a solid support carrying the first nucleosidic or auxiliary residue is placed on a solid support housing. The support is then treated with a deprotectant solution to remove a masking group, generally a DMT-protecting group on a hydroxyl group. The newly unmasked hydroxyl group is then free to react in the subsequent step with the next desired residue in the oligomer sequence. In this instance, the next residue is added as a phosphoramidite monomer that is mixed with an activator used to facilitate the reaction. The newly formed phosphotriester is not sufficiently stable for the remainder of the synthesis and thus is generally oxidized, thiolated, or otherwise stabilized. Before restarting the next cycle, nonreacted species are terminated by the use of a capping reagent. This re-masks the nonreacted hydroxyl group to prevent further growth in the subsequent coupling cycles. Repeating the four steps (unmasking, coupling, linkage stabilization, and capping) iteratively can generate oligonucleotides of varying lengths. The fastidious process of solid-phase oligomeric synthesis can be simplified by the use of solid-phase synthesizers.

In large-scale nucleic acid synthesis using one large column, it is necessary that a length of a support layer (hereinafter referred to as "column length") in a flow path direction, is long or a diameter is wide. However, both the column diameter and support length are limited due to flow distribution and high operating back pressure. An even mass transfer is difficult to achieve in these circumstances.

Accordingly, there is an inherent restriction on viable column size and therefore production size. Accordingly, the typical commercial oligonucleotide length is limited to 15 to 40 Mers.

The demand for oligonucleotides is constantly expanding and there is therefore the desire to have an ability to prepare the highest possible number of oligonucleotides inexpensively, in a short time and with a high quality and yield. The present disclosure describes an improved continuous process and an improved device for the preparation of oligonucleotides and polypeptides that overcomes batch process limitations.

BRIEF DESCRIPTION

Various details of the present disclosure are hereinafter summarized to provide a basic understanding. This summary is not an extensive overview of the disclosure and is neither intended to identify certain elements of the disclosure, nor to delineate scope thereof. Rather, the primary purpose of this summary is to present some concepts of the disclosure in a simplified form prior to the more detailed description that is presented hereinafter.

According to a first embodiment, a method of nucleic acid synthesis is provided. The method employs a device including at least one deprotection unit to carry out a step of deprotection, at least one coupling unit to carry out a step of coupling, at least one oxidation/thiolation unit to carry out a step of oxidation or thiolation, and at least one washing unit to carry out a step of washing. A plurality of reaction vessels, or "pots", for nucleic acid synthesis are moved to the units in accord with a synthesis scheme for a desired nucleic acid sequence and at least two reaction vessels are simultaneously acted upon at several of the units in series.

According to another embodiment, a method of nucleic acid synthesis is provided. The method employs an apparatus for multi-stage synthesis of organic molecules of increasing chain length. The apparatus includes at least one deprotection station to carry out a step of deprotection; at least one coupling station to carry out a step of coupling; at least one oxidation/thiolation station to carry out a step of oxidation or thiolation; at least one capping station to carry out a step of capping, and at least one washing station to carry out a step of washing. Each station includes a suitable fluid reservoir. A plurality of nucleic acid synthesis vessels are moved in parallel to the stations via a conveyor device in accord with a synthesis scheme for building a selected nucleic acid sequence with at least one station performing a reaction requiring a longest time (R) relative to the other stations. At least a majority of the vessels are moved in unison (simultaneously but not necessarily to every station) between the stations according to a set period of time (T), wherein the vessels remain at stations with a reaction time less than R for a multiple of T.

According to a device embodiment of this disclosure, an apparatus for the multi-stage synthesis of organic compounds is provided. The apparatus includes the following in combination: (a) a plurality of reaction vessels; (b) a plurality of fluid reservoirs; (c) valve elements associated with said fluid reservoirs; (d) fluid delivery devices for providing a feed stream from the fluid reservoirs to said vessels; (e) a plurality of devices capable of monitoring a chemical composition of effluent from a plurality of said vessels; and (f) a conveyor having a programmed pattern suitable for sequentially transporting the vessels from fluid engagement with one fluid reservoir to a subsequent fluid reservoir according to the programmed pattern.

According to a further embodiment, an apparatus for multi-stage synthesis of organic compounds is provided. The apparatus includes (a) a conveyor that is moveable on or around an axis, the conveyor hosting a plurality of reaction vessels; (b) a device that moves the conveyor in a step-wise fashion, each incremental step docking each of the vessels at one of a plurality of fluid reservoirs; (c) fluid delivery devices that deliver liquid from the fluid reservoirs to each vessel at each docking station; (d) drain systems that drain liquid effluent from each vessel at each docking station into one of a plurality of designated containers; and (e) a programmable computer that controls the conveyor, the fluid delivery devices; and the drain systems.

According to an additional embodiment, a reactor apparatus for sequentially performing a process of building a biological molecule is disclosed. The apparatus has a plurality of separate reaction vessels, each vessel containing a support to which the molecule can be attached. A plurality of fluid reservoirs capable of containing a fluid for effecting a step of the process are similarly provided. A conveyor individually brings each vessel into a fluid-contact mode with each of the fluid reservoirs. The conveyor can position vessels in sequential fluid contact mode with at least a first fluid reservoir and a second fluid reservoir. The vessels are capable of sequential contact with the contents of each of the fluid reservoirs to achieve the sequential treatment of the molecule. At least one mode of operation of the apparatus allows at least two of the vessels to simultaneously receive a fluid from a single fluid reservoir.

According to another embodiment, an apparatus for nucleic acid synthesis is provided. The apparatus includes at least one detritylation station to carry out a step of detritylation; at least one coupling station to carry out a step of coupling; at least one oxidation/thiolation station to carry out a step of oxidation or thiolation; at least one capping station to carry out a step of capping, and at least one washing station to carry out a step of washing. Each station includes a suitable fluid reservoir and the stations are operated in parallel. The apparatus allows a plurality of nucleic acid synthesis vessels to be moved to the stations via a conveyor device in accord with a synthesis scheme for building a selected nucleic acid sequence of at least 100 Mers.

According to another embodiment, a process for the manufacture of peptides is provided. The process employs a device for multi-stage synthesis in which successive amino acids are brought to a carboxyl activated state and linked successively together at active sites via an end carboxyl group. The device includes at least one detritylation station; at least several stations feeding an aliquot of the appropriate amino acid; at least one station to carry out a step of washing; at least one station to carry out a step of neutralization; and at least one station to carry out a step of coupling. Each station includes a suitable fluid reservoir. The process simultaneously moves multiple peptide synthesis vessels to the stations via a conveyor device in accord with a synthesis scheme for building a selected amino acid sequence. The process positions at least two peptide synthesis vessels such that they are simultaneously acted upon in series at several of the stations.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
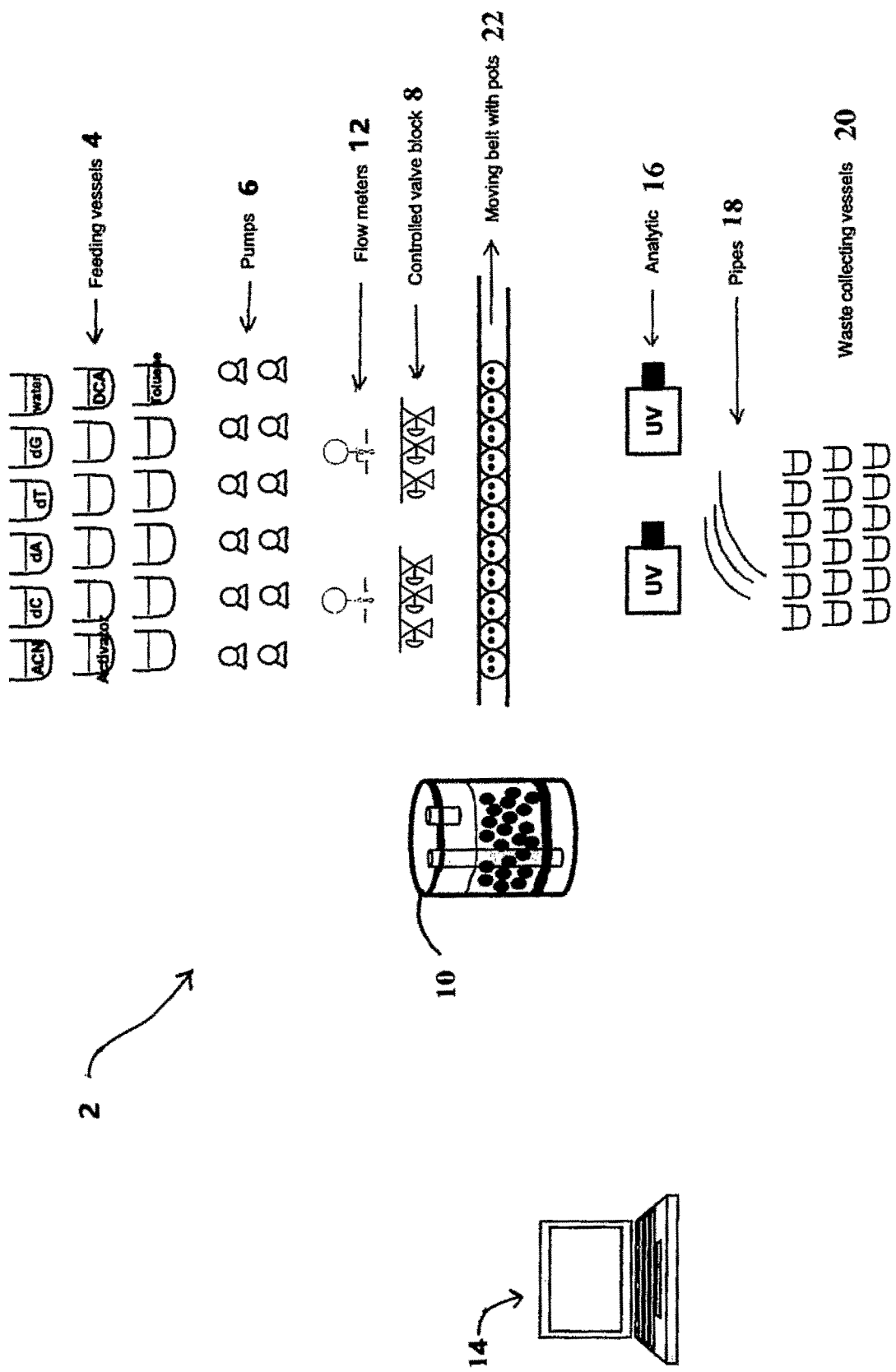
FIG. 1 is a schematic illustration of the system in accord with the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used herein, the terms "about", "generally" and "substantially" are intended to encompass structural or numerical modifications which do not significantly affect the purpose of the element or number modified by such term.

As used herein, certain synthesis steps are described on occasion broadly and on occasion as specific chemical reactions. For example, the word deprotection is used to describe a step of removing a masking group and detritylation is used to described the specific removal of the DMT (4, 4'-dimethoxytrity) group with an acid solution. However, these terms can be used interchangeably to describe a step in oligionucleotide synthesis.

As used herein, the recitation of numerical ranges by endpoints includes all numbers subsumed within that range (e.g. 1 to 5 includes 1, 1.5, 2, 2.75, 3, 3.6, 4, and 5 and the like). Similarly, where multiple ranges are set forth with respect to an item, it is intended that the ranges reflect the various combinations thereof (e.g. 1 to 5 or 2 to 3 also includes the ranges 1 to 3 and 2 to 5, and the like).

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

With reference to FIG. 1, the basic components of the present synthesizer apparatus 2 are illustrated. The components include reactant/reagent feeding vessels 4 containing the liquids for performing the requisite synthesis steps such as washing (e.g. ACN), detritylation (e.g. dichioreactic acid (DCA)/toluene), coupling (e.g. ACN, amidite, activator), thiolation (e.g. pyridine/ACN), capping (e.g. pyridine/ACN/N-methylinidazole (NMI), and post-synthesis wash (e.g. TBA/ACN). The term reactant is used to identify liquids used to grow the oligomer. The term reagent is used to identify liquids used for the preparation and/or activation of the synthesis process. A plurality of unlabeled feeding vessels are shown to demonstrate that the synthesizing apparatus can accommodate any suitable additional feed materials as required by the intended synthesis. Similarly, the illustrated materials may not be required for every synthesis process.

Synthesizer apparatus 2 further includes pumps 6 (or fluid injectors) in fluid communication with the feeding vessels 4. Pumps 6 provide a selected reagent/reactant to valves 8 for delivery to reaction pots 10. The valves can be block valves. Flow meters 12 can be provided to monitor the amount of reagent/reactant introduced. The flow meters and valves can operate in conjunction with a controller such as PLC 14 to provide a fluid delivery control providing precise quantities to each reaction pot at the reaction station(s) more fully described below.

At least one analytical device 16, such as a UV spectroscope, can be associated with the apparatus to monitor a step in the molecule synthesizing process. The operation and monitoring of pump(s) 6, flow meter(s) 12, block valve(s) 8, and analytical device(s) 16 can be performed by a programmed logic controller (PLC) 14. As the skilled artisan will recognize, piping 18 is provided throughout the synthesizer apparatus but to improve viewability is only illustrated in locations where aspects of the inventive concept are better conveyed with its presence. For example, piping can be provided to transport reaction residue from the reaction pots 10 to collection vessel(s) 20. This can allow for the improved recycle of the reagents/reactants, even allowing the collected material to be reused in the process. The synthesizer apparatus 2 includes a large number of individual reaction pots 10 which are associated with a conveyor mechanism 22 such as moving belt. The tops of eleven reaction pots are shown in an array on the conveyor mechanism. It is contemplated that the conveyor mechanism is circular, linear or zig-zag in configuration.

It is contemplated that the components of the synthesizer apparatus, particularly those coming into direct contact with the reagents/reactants can be formed from suitable materials such as stainless steel, polyetheretherketone, and/or polytetrafluoroethylene. It is recommended that the synthesizer apparatus be constructed in accord with FDA regulations, for example, the cGMP's in CFR 21 Part 117. It is further contemplated that the synthesizer apparatus be housed and/ or operated in a controlled environment which can be purged with an inert gas such as argon or a low reactivity gas such as nitrogen.

Each reaction station (see FIG. 1 for example), can include at least one feeding vessel, at least one pump, at least one flow meter and at least one control valve. Suitable piping is of course present to deliver reagent/reactant as appropriate for the particular station. Depending on the need of the reaction and type of reagent, it is envisioned that each station will have the capability of dispersing its associated reagent/reactant liquid at a volume of about 10-1000 ml/minute.

Each feeding vessel in combination with its associated pump(s), piping, flow meter(s), valve(s), analytical device(s), and collection vessel(s) can be considered a reaction or treatment station. Any of the equipment associated with the station(s) may be heated or cooled and/or include a source of pressurized gas for treating a pump, a valve, piping and/or the vessels. The station(s) can each further include one or more of a separation, filtration, membrane extraction and/or chromatography unit.

Turning now to the PLC, a wired or wireless feedback line keeps the PLC 14 in communication with the synthesizer so that it maintains the position of the reaction pots in real time. A position sensor(s) can be provided to monitor the position of the reaction pots. The PLC controls the movement of the reaction pots 10 throughout the reaction protocol, bringing individual pots into fluid connection with the stations according to a programmed synthesis process.

The synthesis can also be controlled by the PLC. Instructions from the PLC can control the timing, volume, flow rate and sequence of reagents/reactants which are introduced to the reaction pots and thus determine the sequence of the oligomer synthesis. These instructions, e.g., to open or close various valves, to move the conveyor/reaction pots, to operate the various pumps, to monitor the flow meters or analytic devices, etc. can be tied to a master instruction associated with the construction of a long-chained molecule of a particular structure.

The PLC can be programmable such that the apparatus can prepare a "batch" of multiple reaction pots of a first long-chained molecule and then reprogrammed to prepare a batch of multiple reaction pots of a different long-chained molecule.

At a plurality (or all) of the stations, an analytic device (or more than one), such as a UV spectrometer can be provided to analyze one or both of the reaction product within the reaction pot 10 or the residue that is collected from the reaction pot 10. In addition, or as an alternative to the UV spectrometer, the system may include a liquid chromatography mass spectroscope (LCMS), a light monitor, a temperature monitor, an infrared monitor, an NMR spectrometer and/or a Raman spectrometer for quality control. The system advantageously allows a reaction pot that demonstrates an unsatisfactory result, such as synthesis error or a molecule that is not fully reacted, to be removed from the conveyor mechanism or otherwise evacuated and excluded from further processing steps. This can contain the impact of a failed reaction step to a single reaction pot rather than contaminate an entire production run.

Figure 2A:
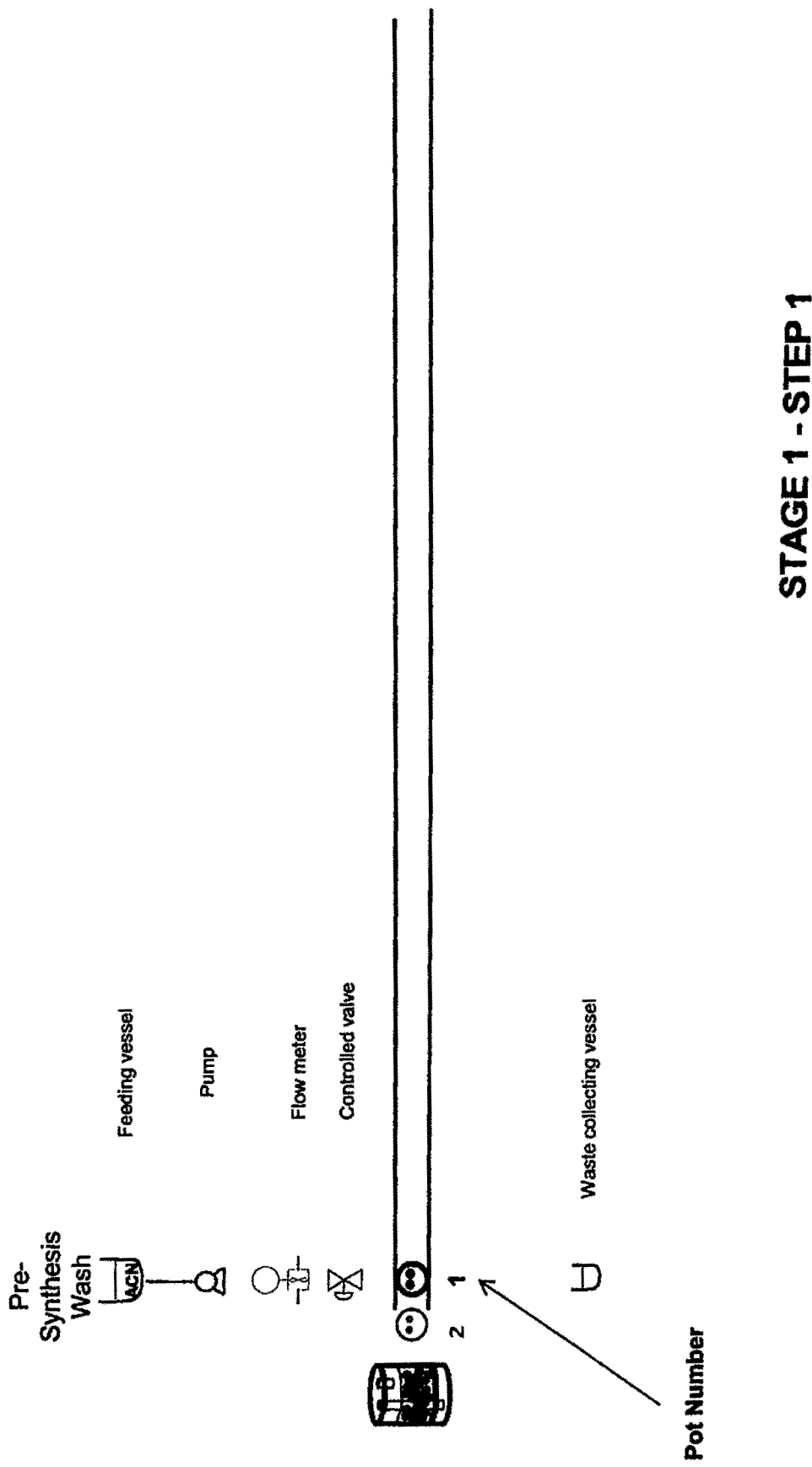
FIGS. 2A-2O provide a schematic illustration of the sequencing aspect of the present disclosure.
Figure 2B:
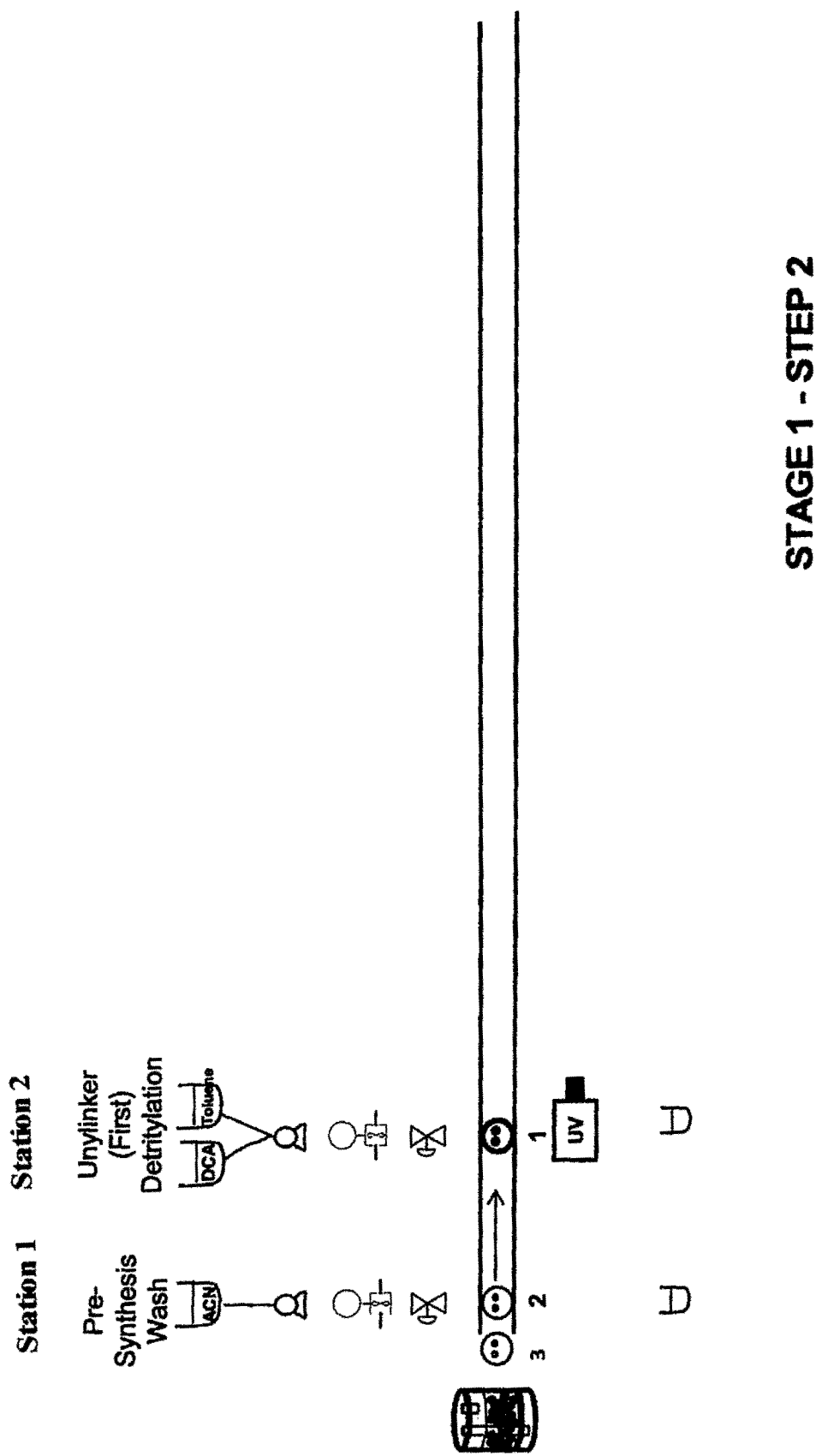
Figure 2C:
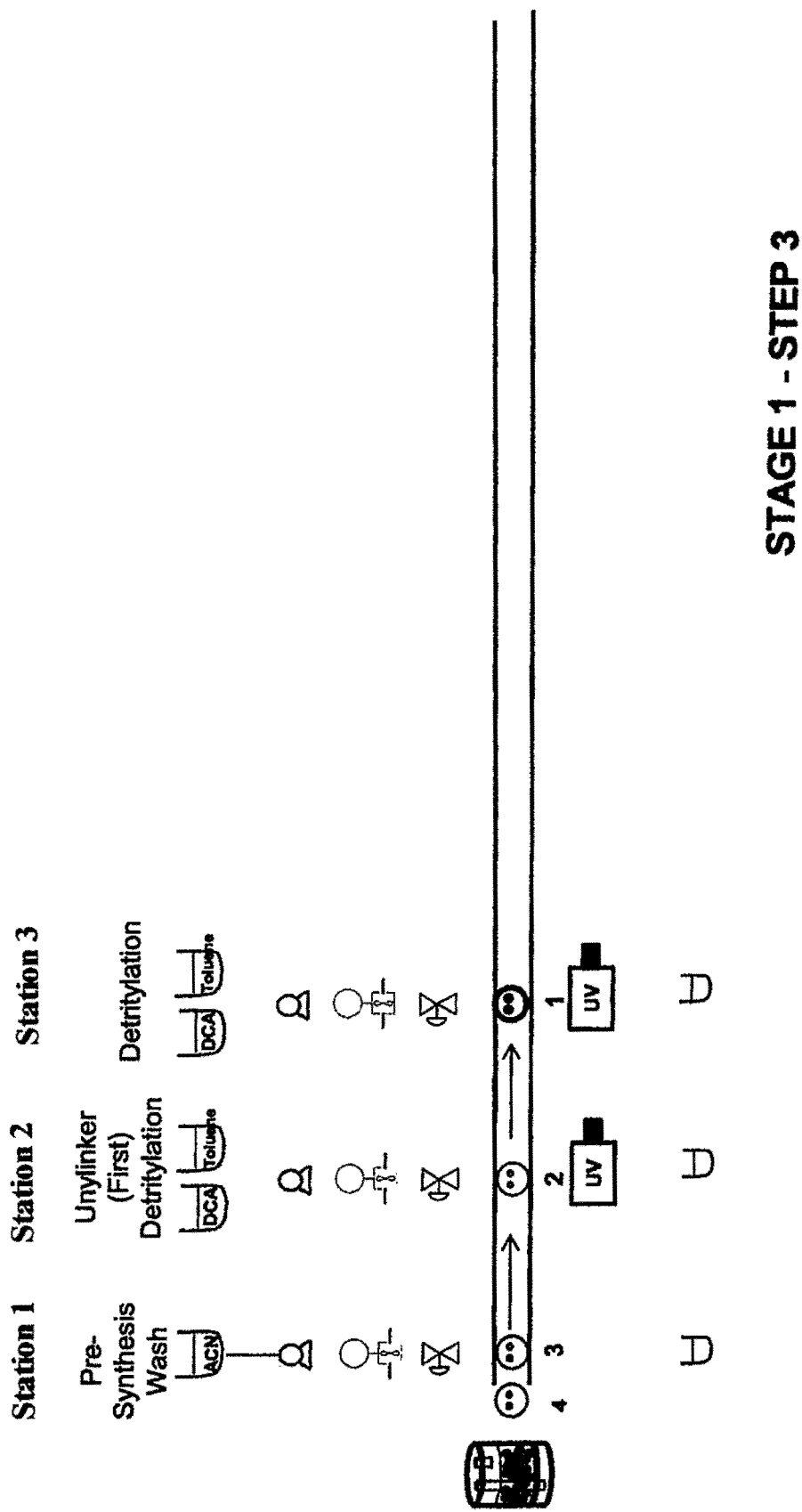
Figure 2D:
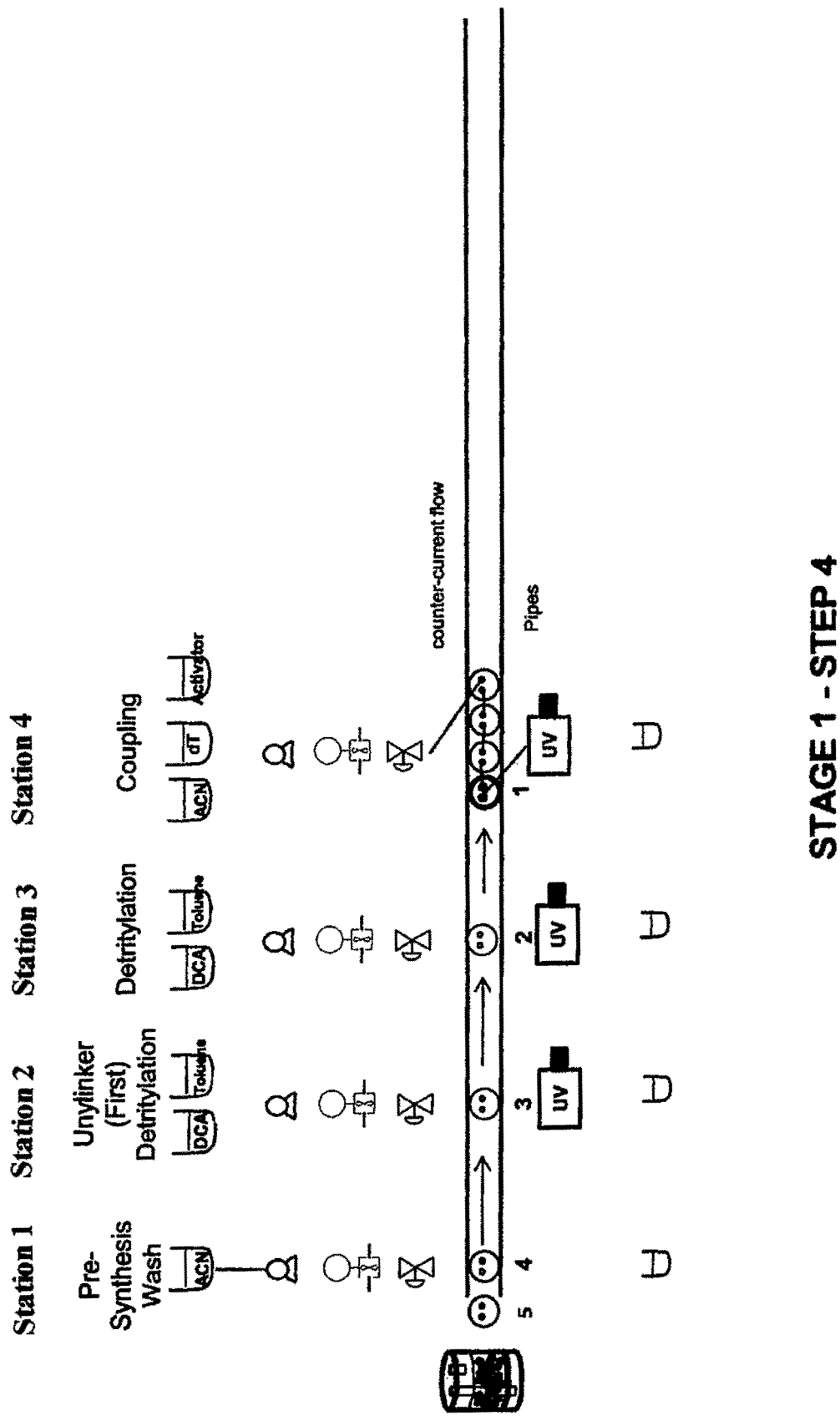
Figure 2E:
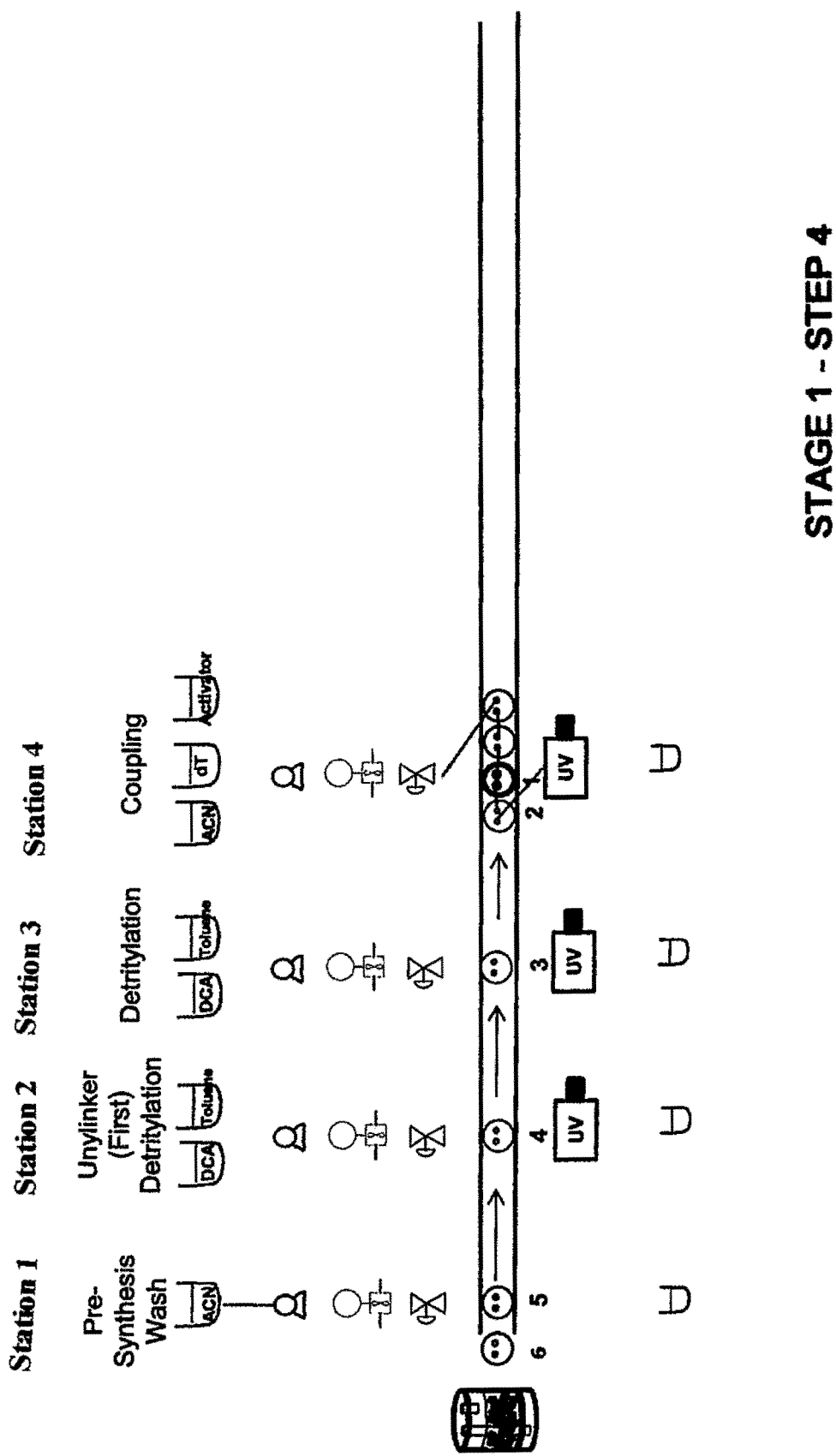
Figure 2F:
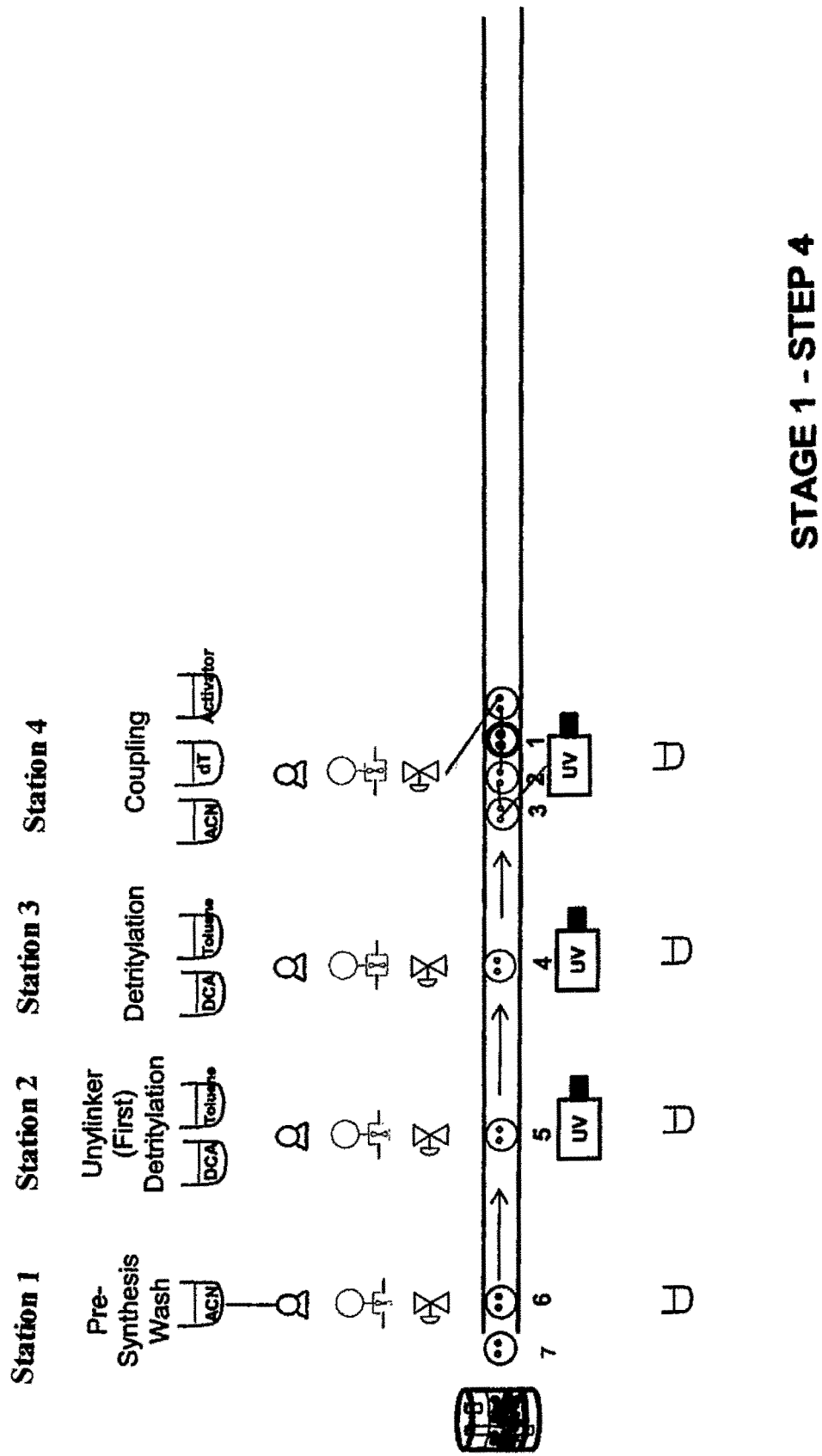
Figure 2G:
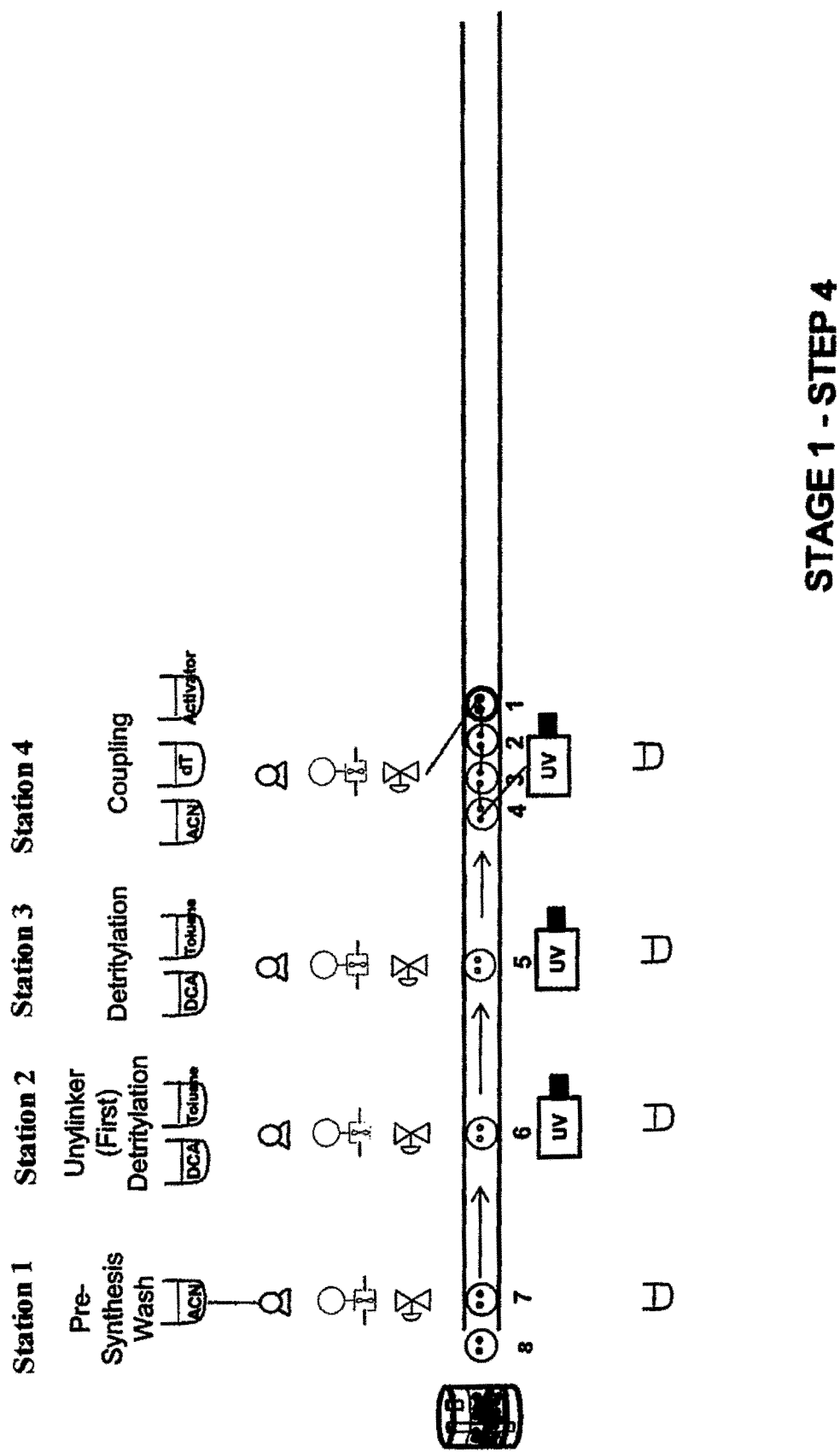
Figure 2H:
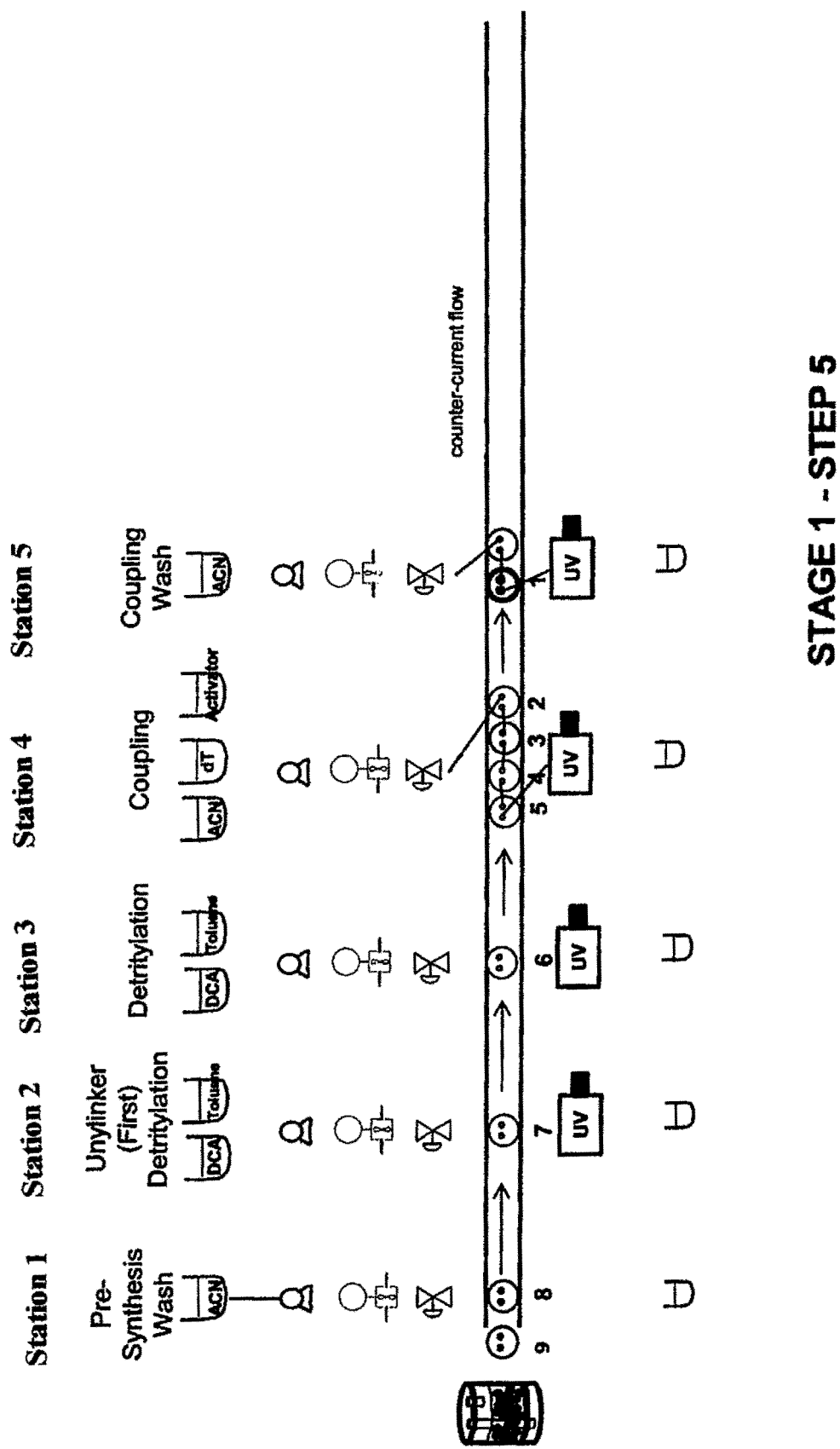
Figure 2I:
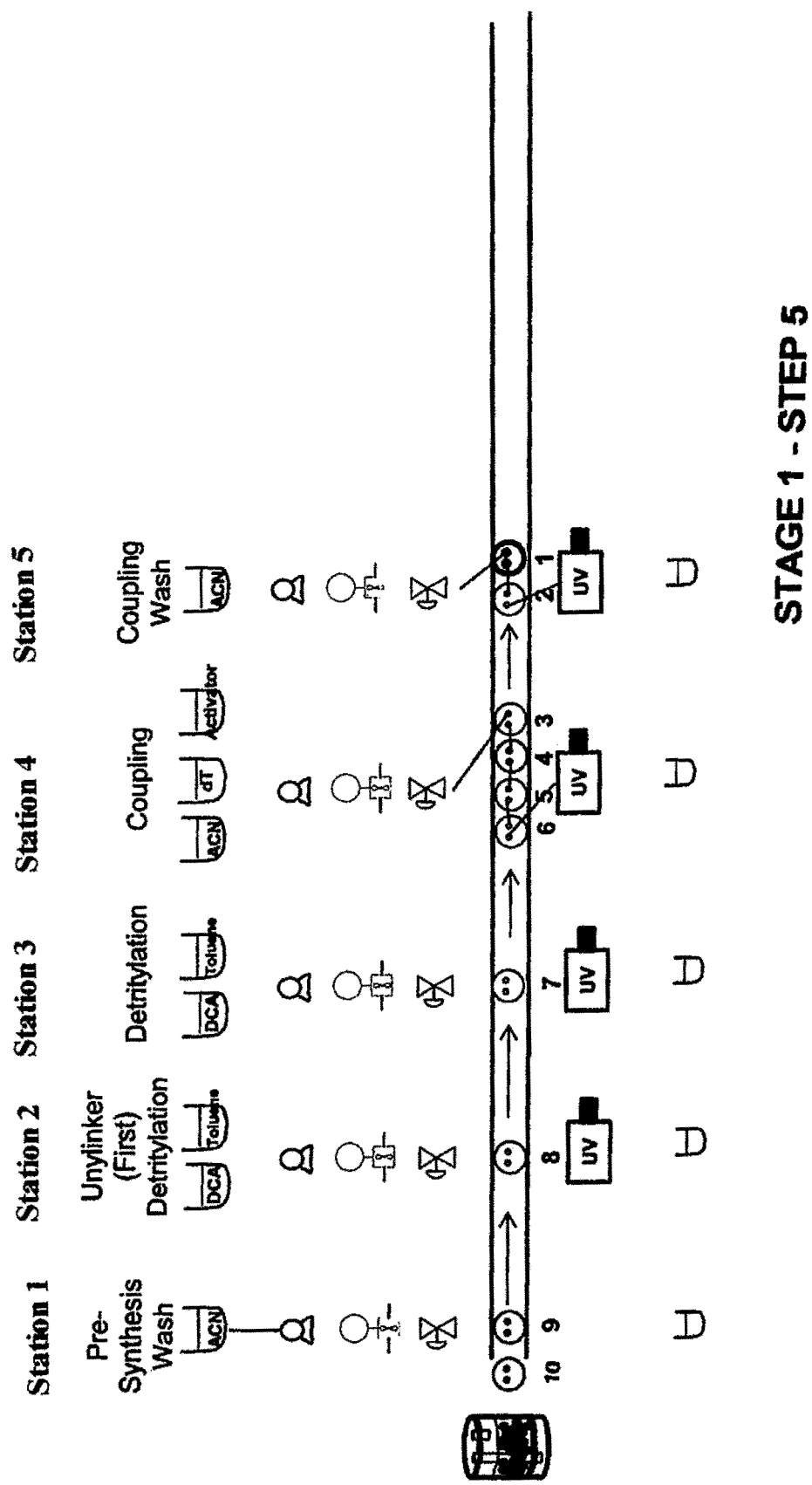
Figure 2J:
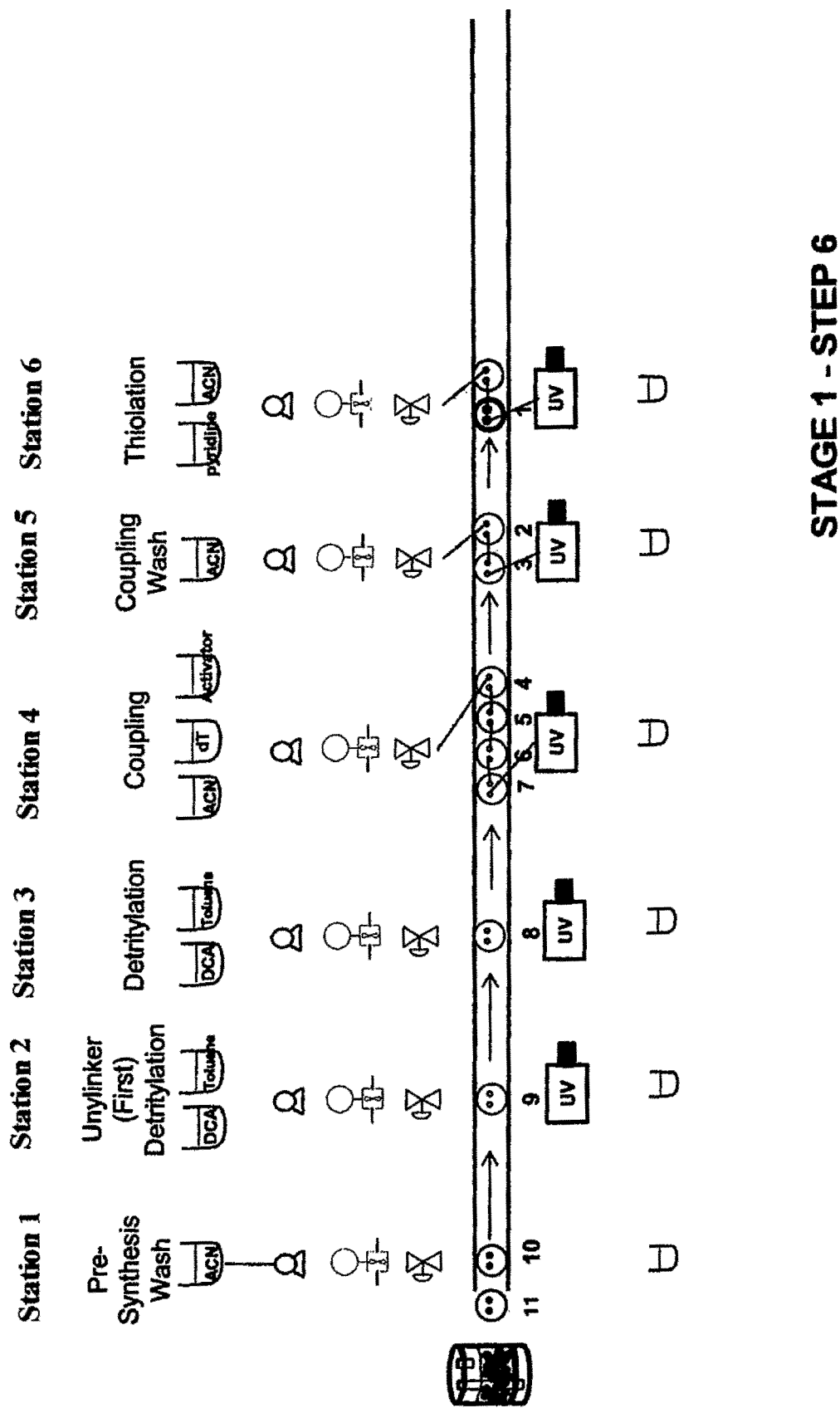
Figure 2K:
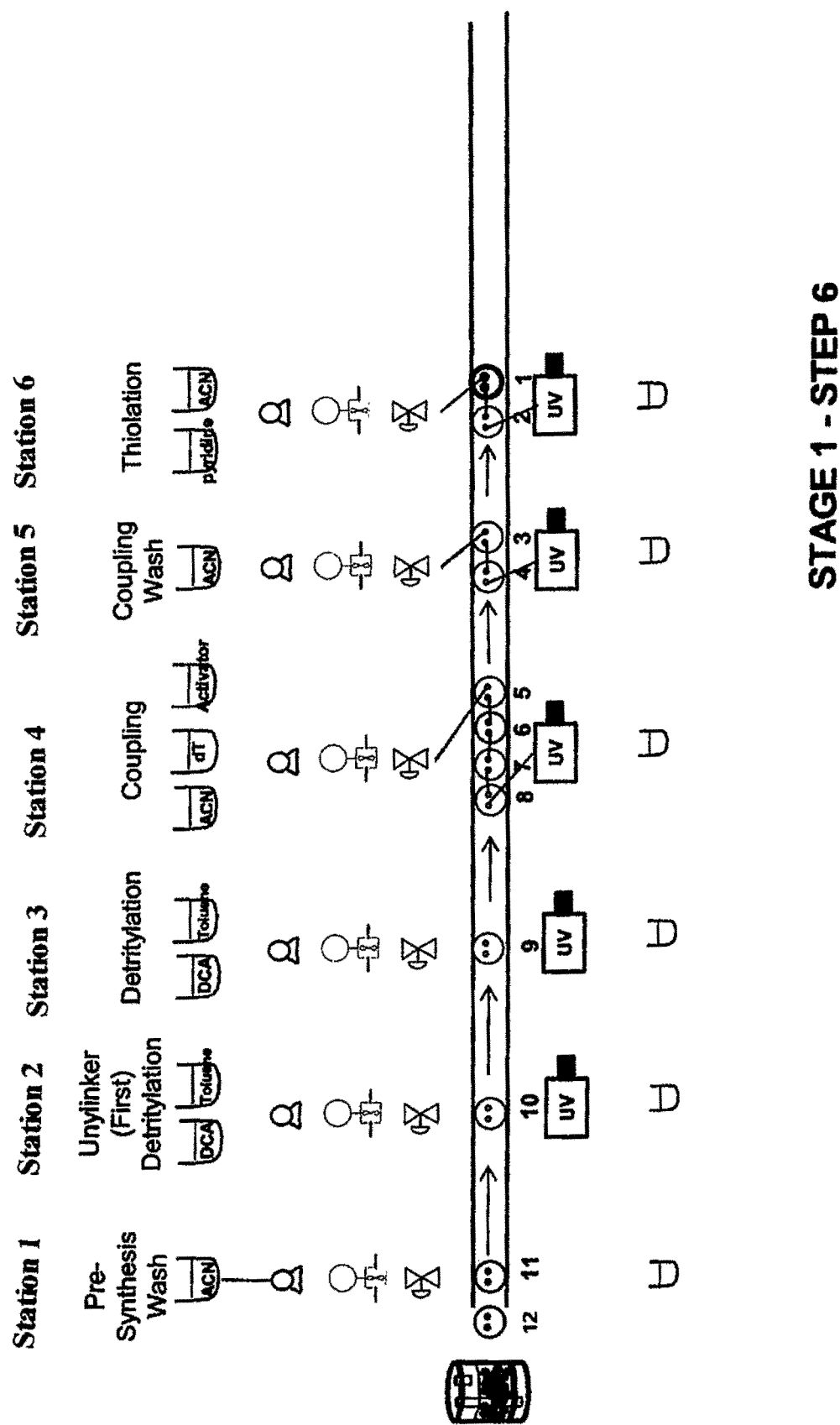
Figure 2L:
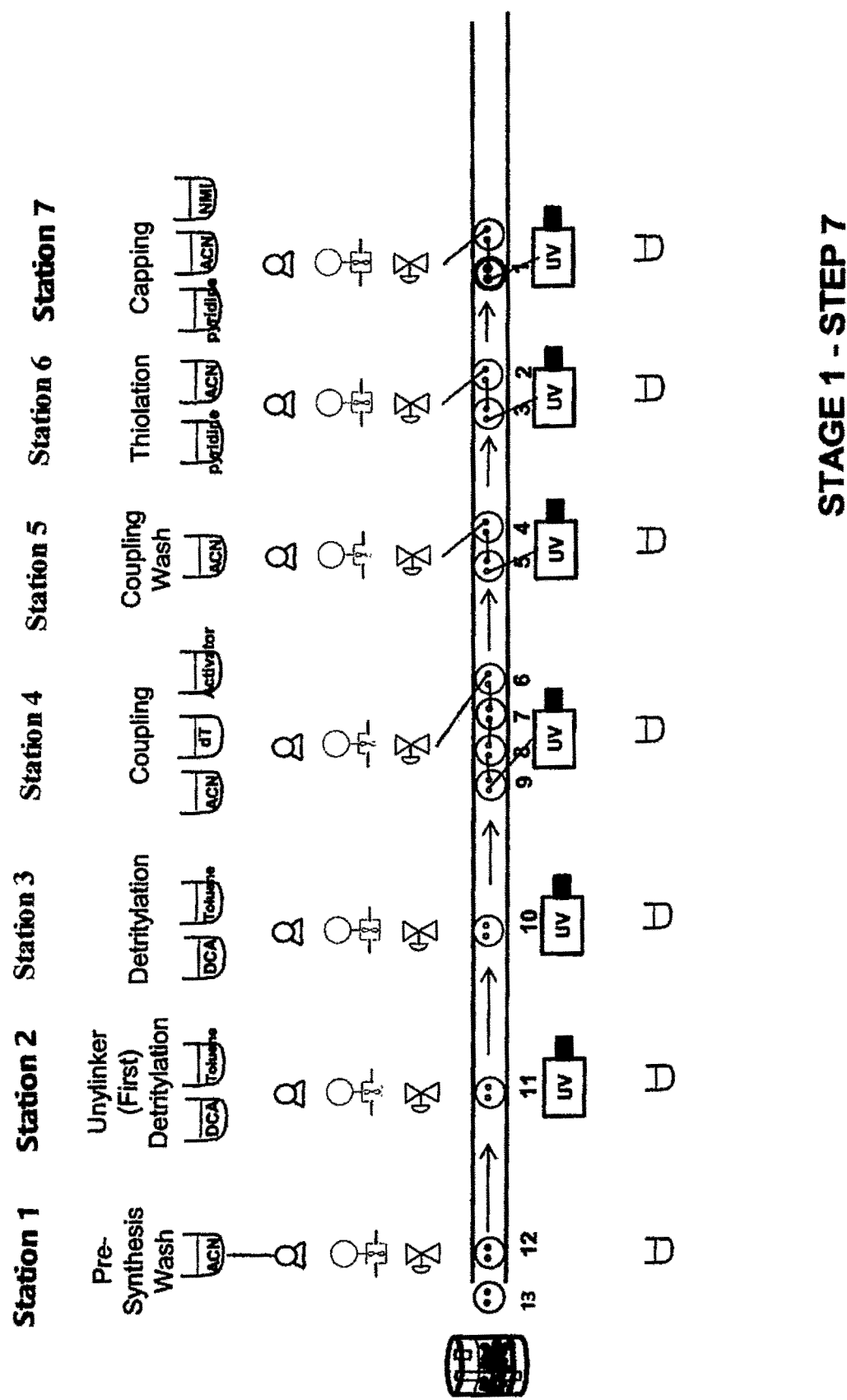
Figure 2M:
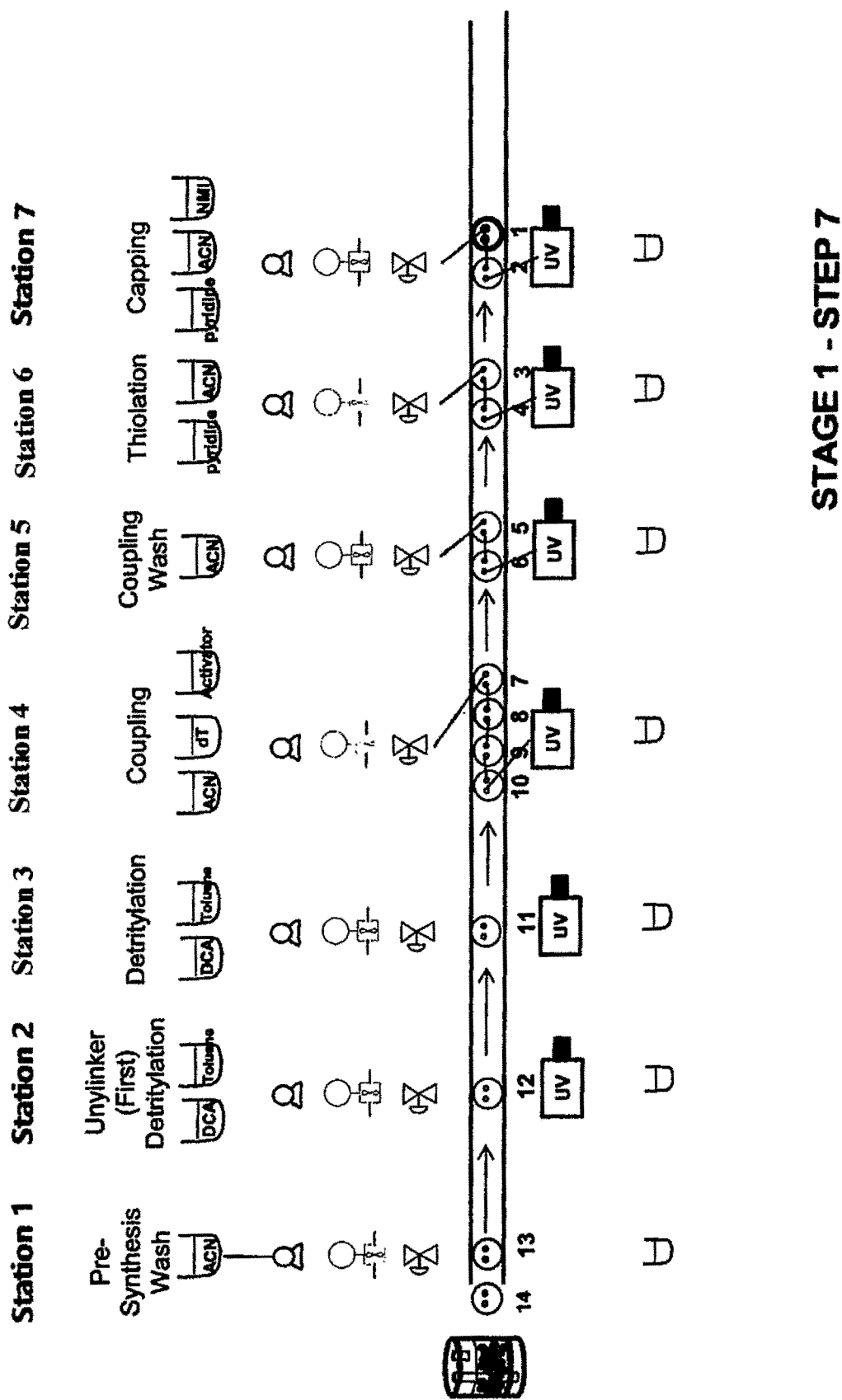
Figure 2N:
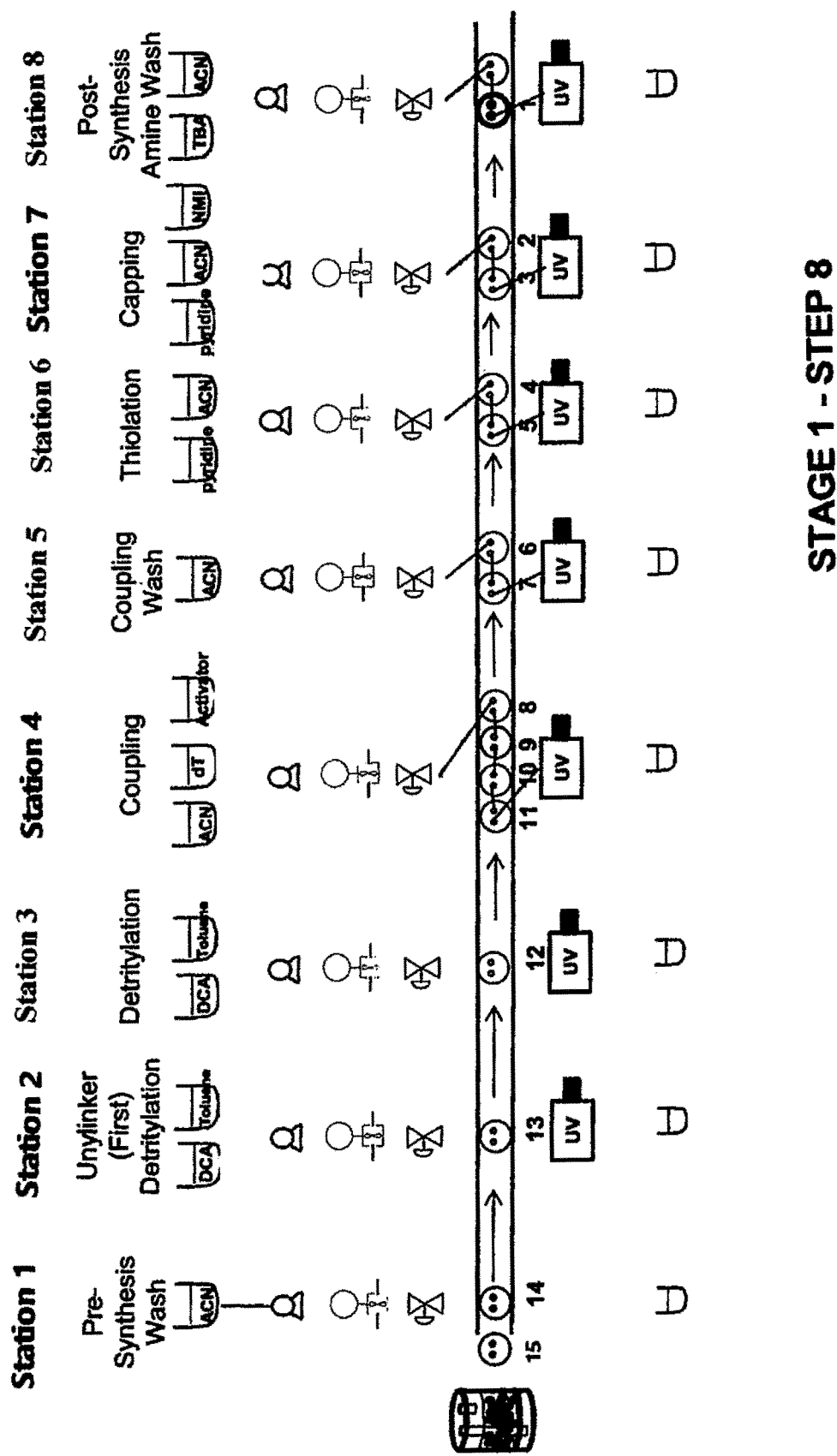
Figure 2O:
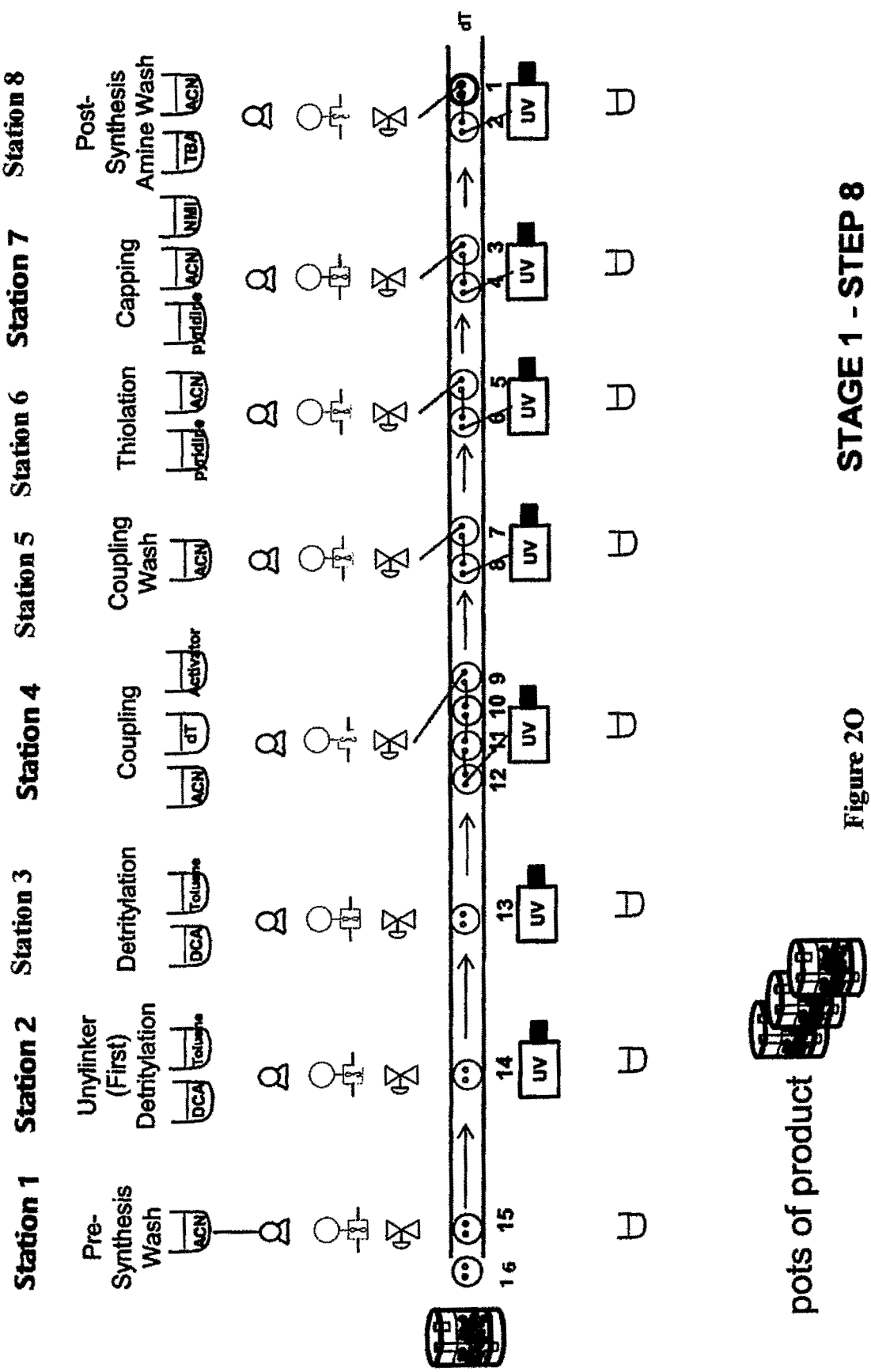

With reference to FIGS. 2A-O, the sequential nature of the synthesis process associated with the present apparatus is depicted. Particularly, at FIG. 2A, a first reaction pot 1 is introduced to a first station (pre-synthesis wash). Reaction pot 2 is positioned to be taken up by the conveyor mechanism next.

The illustrated sequence of steps is of course exemplary only. Moreover, each step is not required nor necessarily performed in the precise order illustrated. For example, an amino wash at the end of each stage may not be necessary. Similarly, the exemplified steps are not required to be performed using the listed chemicals. Rather, alternative fluids are known in the art which are capable of performing a similar/identical function.

Reaction pot 1 (and the subsequent pots) can include a support such as NittoPhase® HL. A frit or filter cloth can be provided in the reaction pot to host the support. The support can include particles having a size less than traditional (for example less than 80 μm or even 40 μm or even 1 μm or 0.3 μm) because pressure loss is relatively low in view of the relatively small size of the reaction pot. It is noted that liquid phase synthesis is also contemplated.

Reaction pot 1 is first associated with a station for pre-synthesis wash where it receives ACN. A waste collecting vessel is linked to the reaction pots at the pre-synthesis station to recover excess ACN for recycle. Each station can have its own pump for introducing liquid from a feeding vessel. Each station can also include its own flow meter to control the rate of fluid introduction to match the kinetics of the reaction/treatment occurring at that station. Each station can further include its own control valve (or series of control valves) to assure delivery of a sufficient volume of fluid to the reaction pot to complete the associated reaction/treatment. Moreover, multiple control valves may be provided at stations allowing multiple reaction pots to be treated simultaneously.

Turning now to FIG. 2B, reaction pot 1 has transitioned to a second station where detritylation is performed while reaction pot 2 has entered the conveyor mechanism and is positioned at the first station for pre-synthesis wash. Each of reaction pots 1 and 2 can be positioned at their respective synthesis stations for at least approximately the same period of time. The second station may operate with a flow rate and/or volume that differs from the first (or a subsequent) station. This is equally true for the other stations of the apparatus.

The second station can include a UV spectroscope 16 or other analytic device to allow assessment of the state of reaction pot 1 and/or its residue. A separate waste collecting (recycle) vessel is provided at the second station for recovery and potential recycle of excess reagent. This is equally true for the other stations of the apparatus.

Turning now to FIG. 2C, the conveyor mechanism has moved reaction pot 1 to a third station for a second detritylation stage using a different concentration of DCA/toluene feed. At least substantially simultaneously, reaction pot 2 has been moved by the conveyor mechanism to the second station for a first detritylation treatment and reaction pot 3 has entered the apparatus at the first station for pre-synthesis washing. A UV spectroscope has been provided to assess the contents of reaction pot 1 and/or its residue at the third station.

Advantageously, because the same pump, piping and valve apparatus are being used at each station with the same reagents, there is no requirement for discharge of liquid remnants or cleaning between synthesis steps. This advantage also extends to the transition from a synthesis sequence to form a first molecule to a synthesis sequence configured to form a second molecule. This improves the processing speed and reduces waste.

Turning now to FIG. 2D, reaction pot 1 has reached a fourth station for coupling while reaction pot 4 has been picked up by the conveyor mechanism and transported to the first station for pre-synthesis. Each of reaction pots 1-4 are acted upon at their respective station at least substantially at the same time. The coupling station is illustrated with three reaction pots (three reaction pots were shown for illustration purposes only) that could have preceded reaction pot 1. A counter-current flow is used to provide exceptional efficiency in association with introduction of the relatively expensive phosphoramidite. Moreover, phosphoramidite waste can be less than during traditional batch processing.

The reaction pots at the coupling station can move at the same time as the other reaction pots in the array yet remain in fluid communication with the coupling station for multiple active periods (i.e. the time the reaction pots receiving fluid from the station). The counter-current flow of liquid allows multiple reaction pots to be treated simultaneously. In FIG. 2D, four reaction pots simultaneously receive the amidite reaction feed thymine, ACN and activator (such as ethylthio-1 H-tetrazole (ETT)). The amidite feed can be at a concentration in excess of what a single reaction pot would require. The amidite may be introduced to the first reaction pot at greater than a 3:1 stoichiometric requirement. For example, phosphoramidite can be added in an amount between from about greater than 0 to 5.0 or about 1.5 to 3.0 of reaction capacity based on support volume. The excess amidite travels to the serially linked reaction pots. In this manner, unreacted amidite from one serially linked reaction pot will flow to the next reaction pot and be picked up for molecule building, resulting in a significant reduction in phophoramidite loss relative to batch processing.

In certain synthesis processes, it may be desirable to provide an intermittent and/or pulsed washing feature to the coupling procedure. Moreover, the pulsed washing can be used to unstick unreacted amidite that may otherwise not easily flow to downstream reaction pots. The washing can be performed by a liquid such as ACN or a gas such as $N_2$ or a combination thereof.

The introduced amidite is added to the growing molecule. By serially linking the reaction pots and moving then sequentially up the counter-current chain, the process ensures appropriate molecule building by exposing a reaction pot to the highest stoichiometric concentration of amidite at the last position of the coupling station. In short, "residual" amidite from one reaction pot is used to "pre-treat" subsequent reaction pots, reducing waste. It is also noted that the counter-current methodology used in association with the amidite feed station is equally suitable for use at any or all of the other stations of the synthesizer apparatus.

FIGS. 2E-2G demonstrate that when the reaction pots are moved downstream on the conveyor mechanism, new reaction pots 5, 6 and 7 join the serial progression of reaction pots while reaction pots 2, 3 and 4, join reaction pot 1 in the counter-current flow arrangement at the thymine coupling station.

FIGS. 2H and 2I illustrate, respectively, how reaction pot 1 and reaction pot 2 move sequentially to a coupling wash station. The coupling wash station can also be a counter-current flow configuration. An example wherein two reaction pots are receiving coupling fluid in series is illustrated. Of course, more than two reaction pots could be serially linked. As is apparent, the reaction pots have been followed sequentially with new reaction pots (reaction pots 8 and 9).

Turning now to FIGS. 2J and 2K, reaction pot 1 and reaction pot 2 have sequentially moved to a station for thiolation (pyridine/ACN). As is apparent, the reaction pots are followed sequentially by new reaction pots (reaction pots 10 and 11).

FIGS. 2L and 2M illustrate, respectively, reaction pot 1 and reaction pot 2 being sequentially moved to a capping station (pyridine/ACN/NMI/AC20), again using a counter-current flow configuration. As is apparent, the reaction pots are followed sequentially by new reaction pots (reaction pots 13 and 14).

FIGS. 2N and 2O illustrate, respectively, reaction pot 1 and reaction pot 2 being sequentially moved to a station for a post-synthesis amine wash. The reaction pots in the synthesis process are followed sequentially by new reaction pots (reaction pots 15 and 16). After completion of the post-synthesis amine wash, an exemplary first synthesis stage can be considered complete, yielding a multitude of reaction pots containing an in-process molecule with a first oligeonucleotide unit dT.

Figure 3:
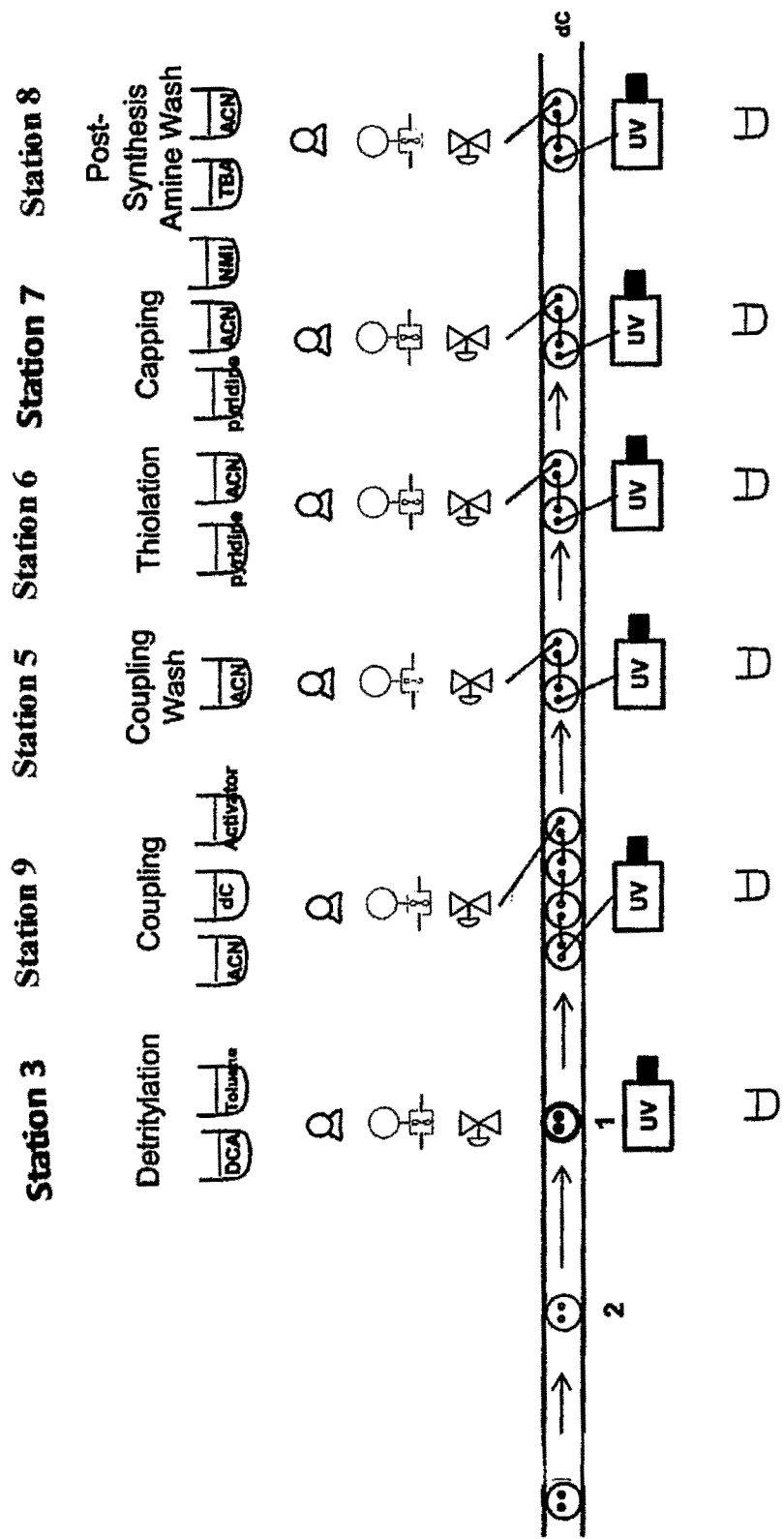
FIG. 3 provides a schematic illustration of an abbreviated second sequencing step suitable for following the process of FIG. 2.

FIG. 3 illustrates a second synthesis stage wherein the reaction pots from the first synthesis stage are received and further processed. Advantageously, the same stations as used in stage 1 can be used in stage 2. In fact, it is envisioned that the stations will be simultaneously performing stage 1, stage 2, stage 3, etc. Certain steps such as pre-washing and a first detritylation step may not be required for the second synthesis stage. For clarity sake, it is noted that the stations 3, 5, 6, 7, and 8 from stage 1 are being reused in stage 2 and station 9 to provide cytosine is added to the stage 2 protocol.

Moreover, although any amidite can be processed in the second synthesis stage, the synthesis of cytosine is shown. This can be achieved by the addition of a cytosine feeding station 9. It is also contemplated that a complete station (feeding vessel, pump, flow meter, valve block, analytic device and residue collection device) is provided for cytosine introduction. Further stations can be added for each amidite being included in the molecule. Notably, since the synthesizer apparatus can be configured to form any number of oligeonucleotides, it will likely be equipped with a station for each commonly employed amidite or all amidites.

Figure 4:
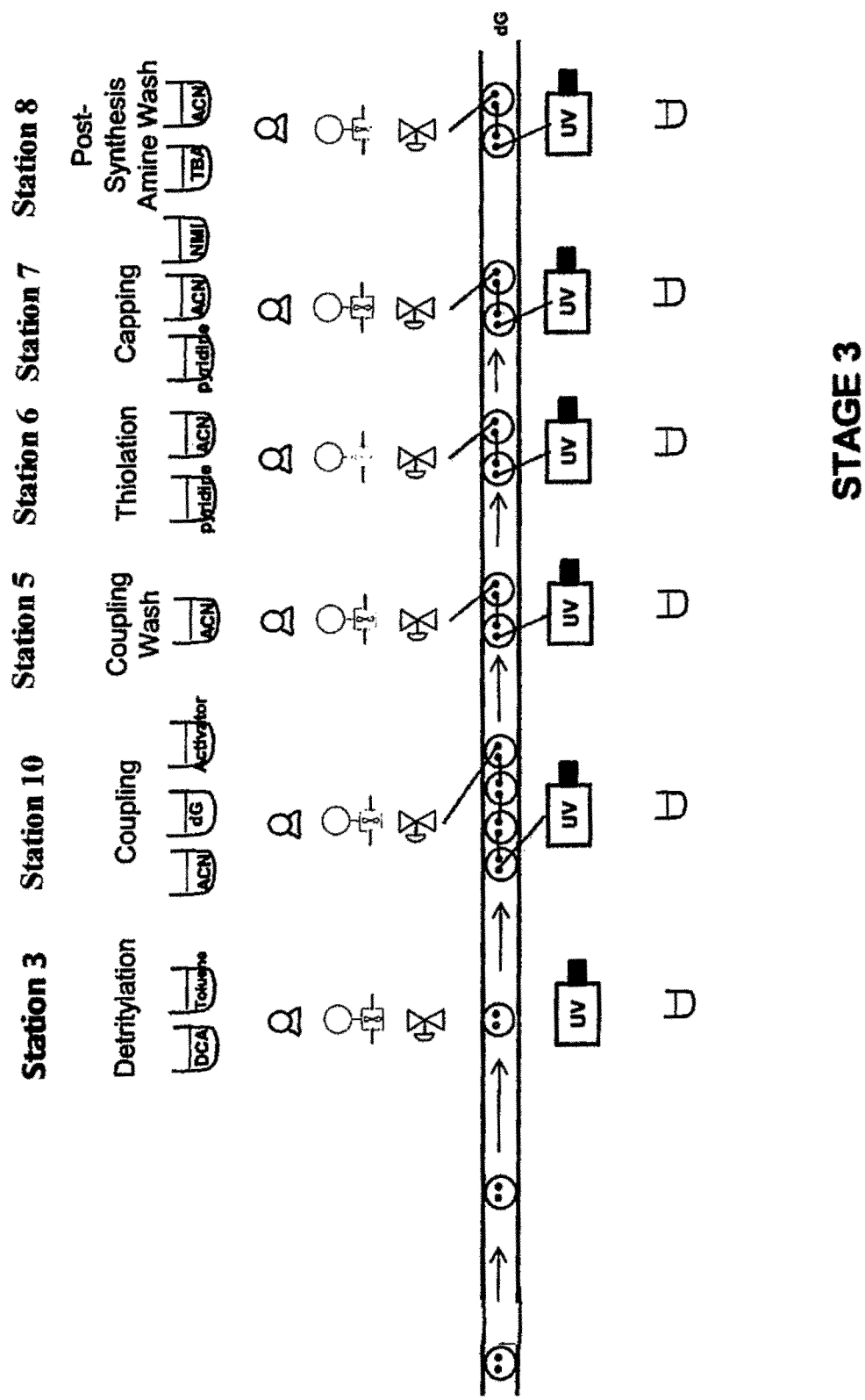
FIG. 4 provides a schematic illustration of an abbreviated third sequencing step suitable for following the process of FIG. 3.
Figure 5:
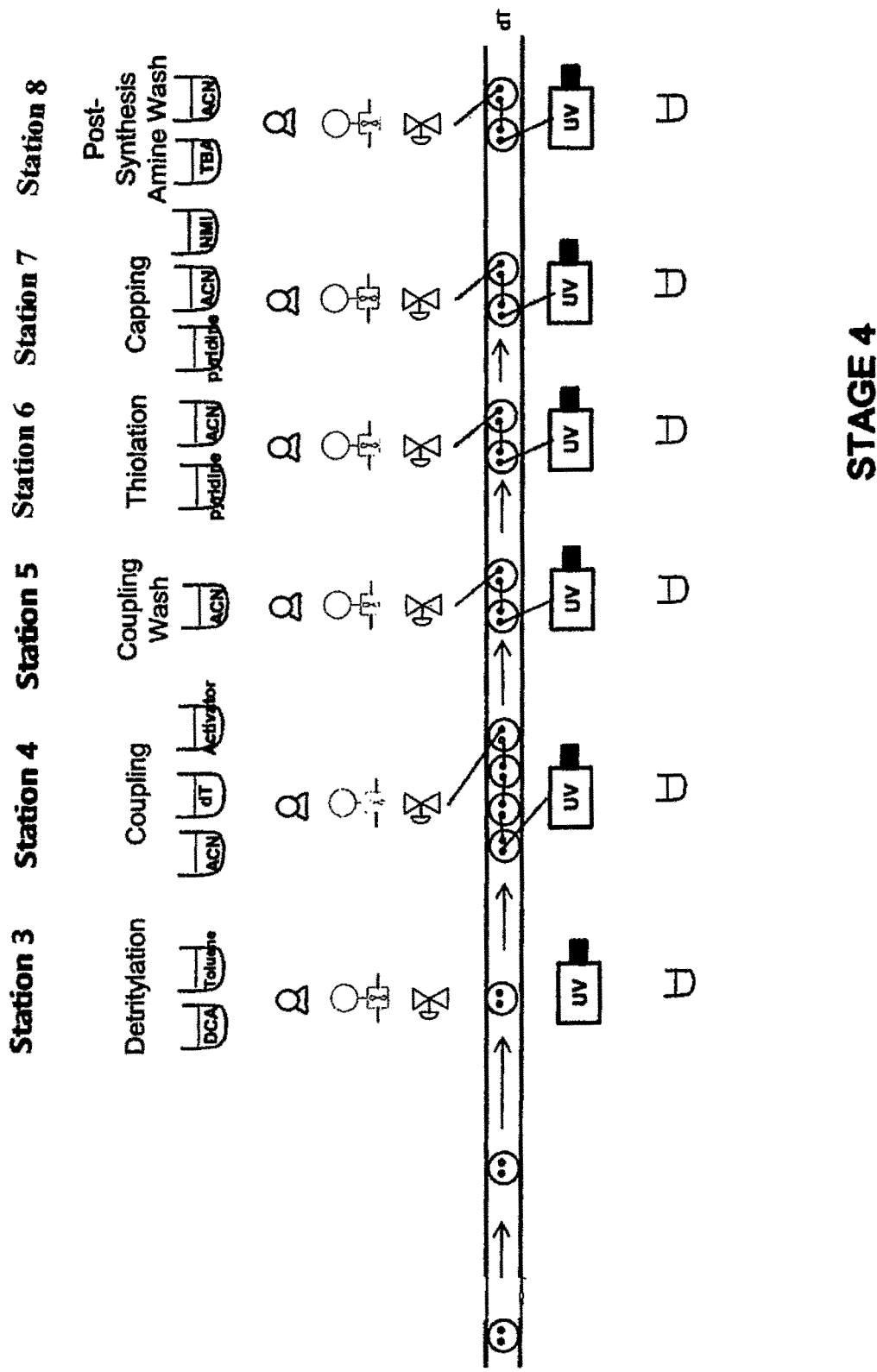
FIG. 5 provides a schematic illustration of an abbreviated fourth sequencing step suitable for following the process of FIG. 4.
Figure 6:
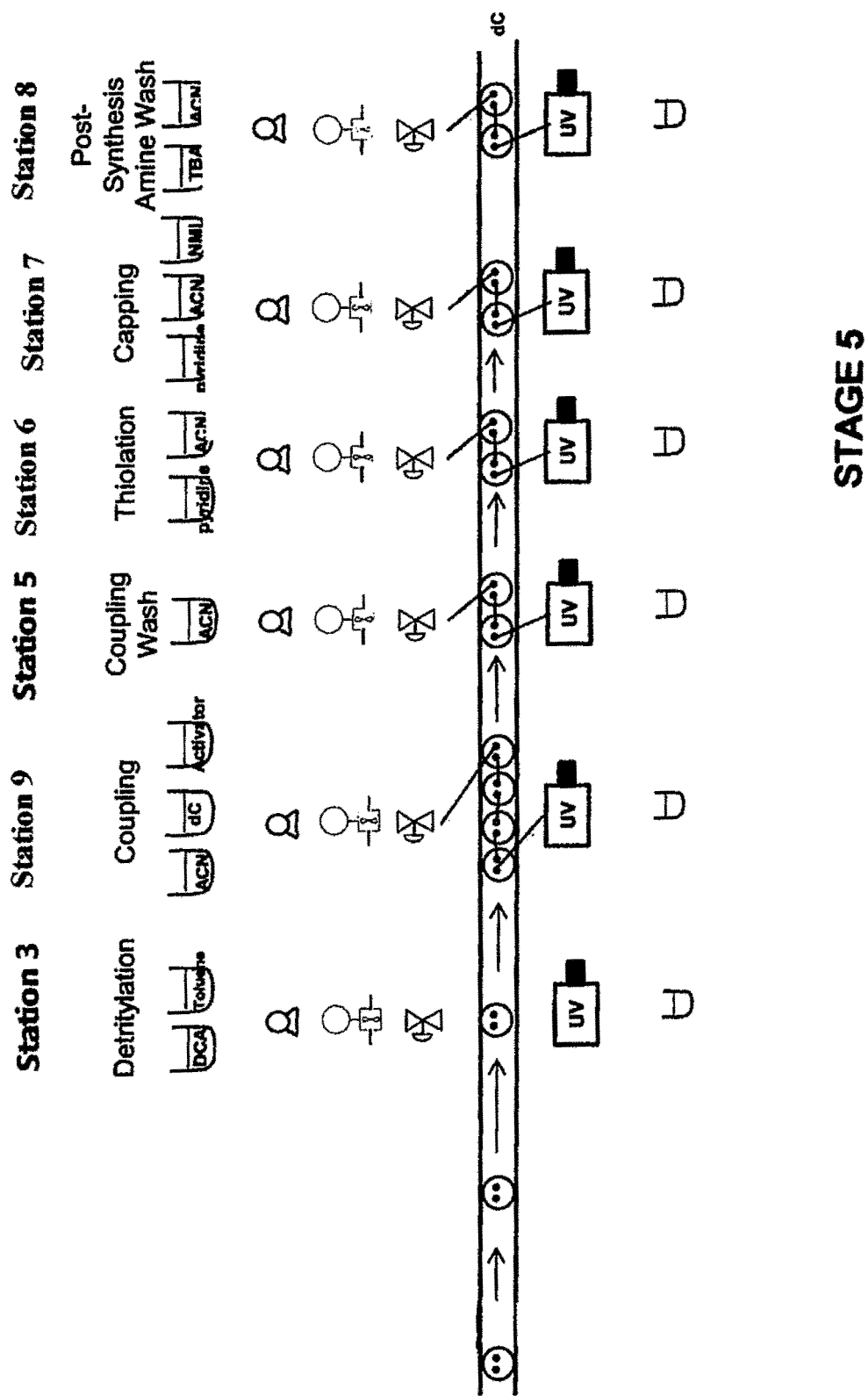
FIG. 6 provides a schematic illustration of an abbreviated fifth sequencing step suitable for following the process of FIG. 5.

FIGS. 4, 5 and 6 illustrate further synthesis stages being employed to build polymer length, wherein the reaction pots of the prior stages are sequentially introduced to add amidite(s). Station 10 is provided to feed the new amidite dG. However, pump (4) is used again for the second introduction of dT at stage 4. Station 9 is used for the second introduction of dC at stage 5. While FIG. 5 represents a new step in the synthesis process it also constitutes a repeat of step 1 in the protocol. FIG. 6 represents a repeat of stage 2 of the sequence protocols.

This reuse of amidite stations can be repeated as necessary to build a molecule of desired structure and length. In this context, it is envisioned that molecules of between 2 and 300 Mers, or at least 100 Mers, or greater than 200 Mers, or greater than 300 Mers can be produced (base pairs is the appropriate reference when considering polypeptides). After synthesis of the desired molecule in the multiple reaction pots, the contents thereof can be combined in a larger storage container. The combined contents can be processed in accord with traditional oligonucleotide manufacturing/purification techniques.

The system can include in excess of 15 conveyor arrays processing in excess of 100 reaction pots to achieve a desirable length of molecule. Generally speaking, it is envisioned that each conveyor array will receive multiple (e.g. at least 7) reaction pots.

It is envisioned that the reactor of the subject disclosure can have numerous (e.g., more than 20) reactions in a row and that multiple rows (e.g., more than 20) can be provided. In this context, over 400 reactor pots can be simultaneously acted upon, with the majority of pots being at a different stage in molecule building. In general, an exemplary reactor could have 5 to 25 reaction stations and include 5 to 10 rows.

Figure 7:
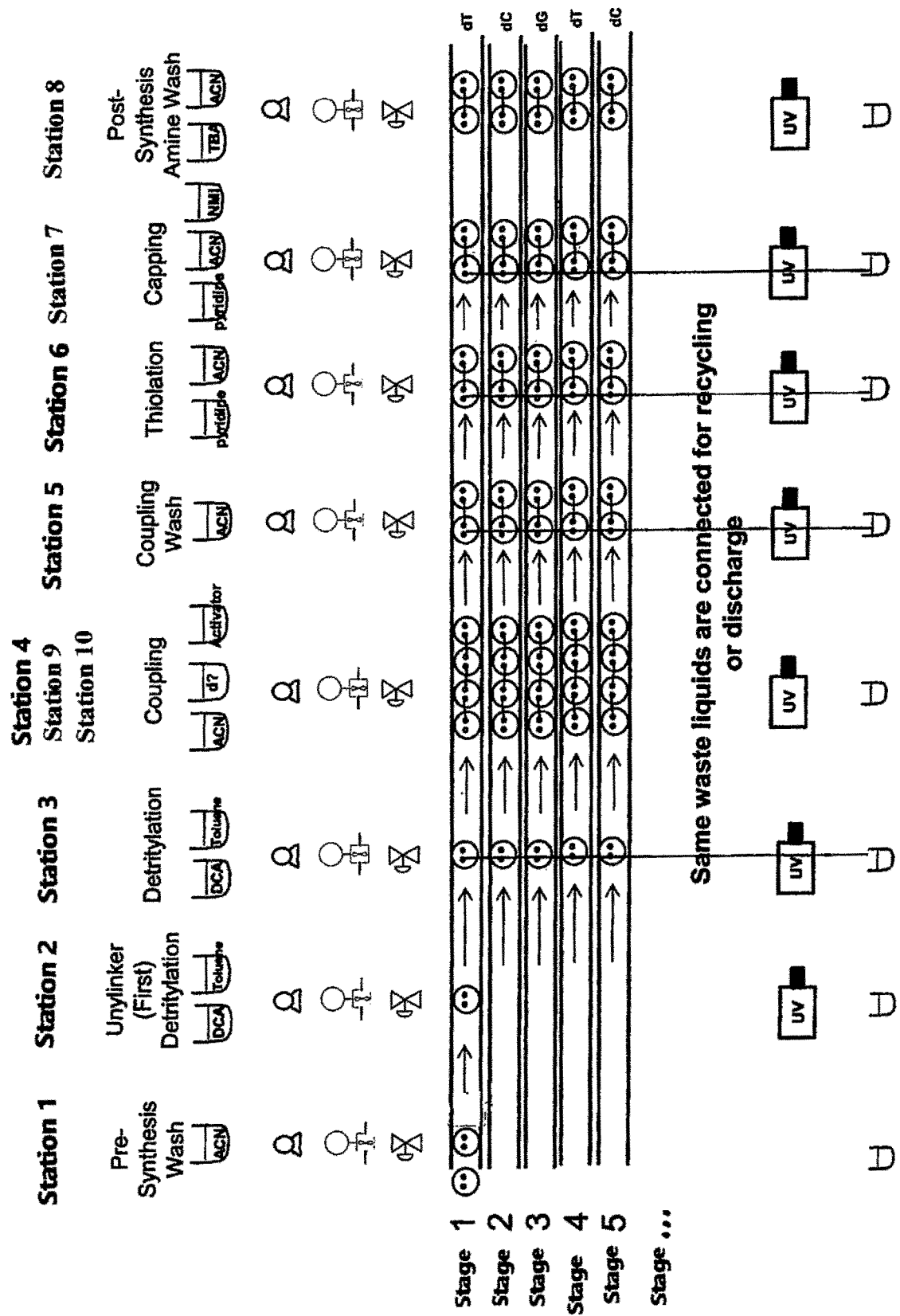
FIG. 7 provides a schematic illustration of each of the first through fifth sequencing steps as performed in parallel.

With reference to FIG. 7, the efficiencies provided by the present synthesizer apparatus are visible. For example, it is feasible to provide a single feeding vessel and feed equipment (a station) for each step of the synthesis sequence. By providing separate pumps, flow meters, valves, and piping, a single reservoir can supply reaction pots in either of stage 1 to 5 (or beyond). Similarly, a single amidite reservoir can supply the amidite to different steps in the synthesis sequence (for example, thymine to stages 1 and 4).

Furthermore, it is contemplated that the reagent/reactant can be supplied at different concentrations at different steps of the molecule synthesis. For example, it may be desirable to introduce more activator at stage 5 than at stage 1. Similarly, it may be desirable to add a lesser concentration of coupling wash to later stages in the synthesis process. Similarly, the amount of amidite introduced can be varied depending upon the number of reaction pots linked in series at a single reaction station.

Further benefits result from using each reaction station with only one type of reactant/reagent because the pumps, flow meters, valves are not required to be cleaned between steps in the synthesis process. Similarly, the equipment is not required to be emptied between reaction stages. In this context a single station (thiolation for example) can be used to treat multiple reaction pots at difference stages of polymer synthesis.

It is also contemplated that the synthesizer apparatus includes one of a cleavage, deprotection, separation, filtration, membrane extraction and/or chromatography unit at one or a plurality of the stations.

Figure 8:
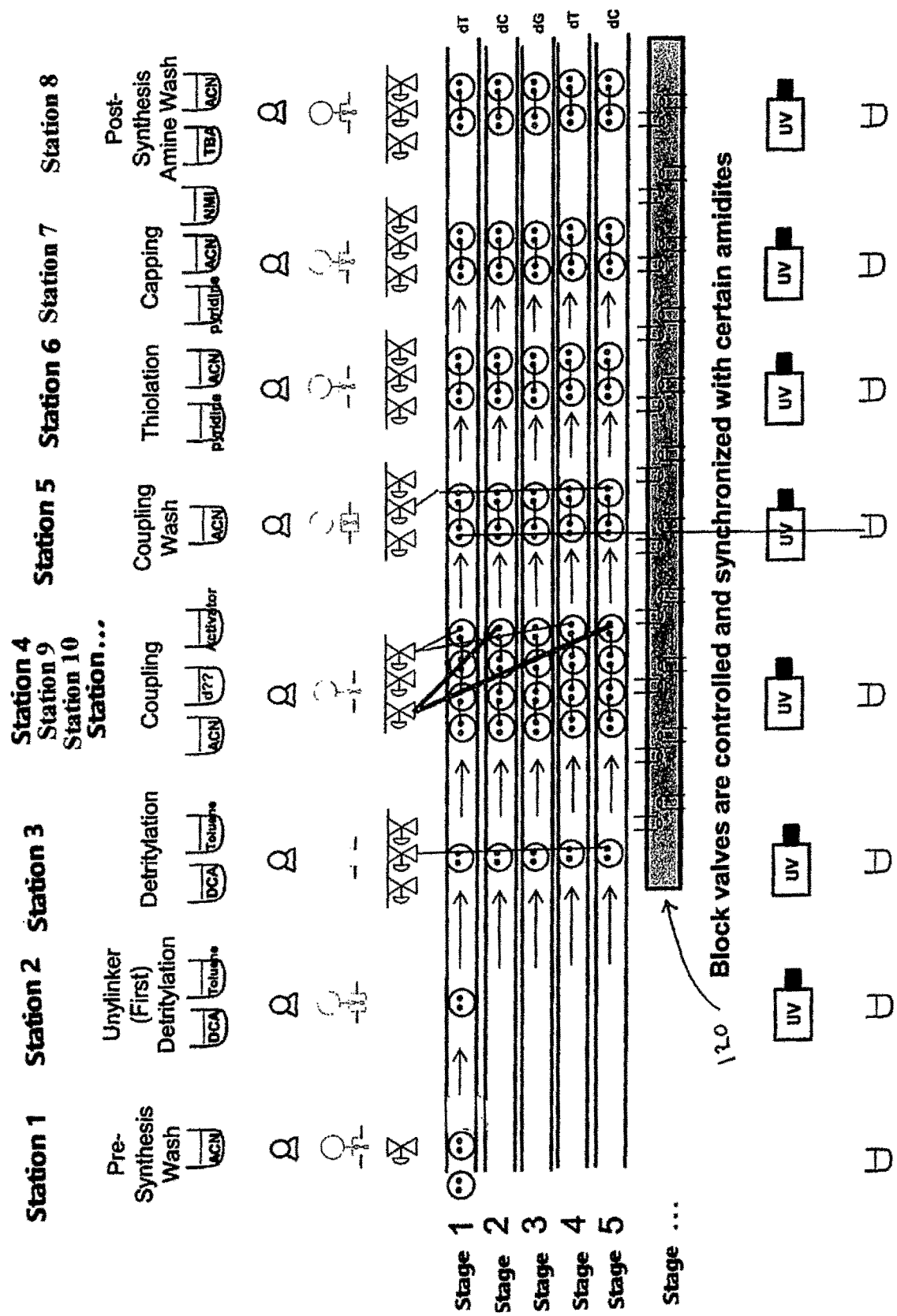
FIG. 8 provides a schematic illustration demonstrating the integration of multiple stages.

FIG. 8 demonstrates that a single pump can be used for each station with the exception of the coupling station(s), wherein a pump can be supplied for each amidite being employed. Furthermore, several stations can include a multi-block valve having the ability to deliver several feed streams simultaneously. Taking the coupling station as an example, the multi-block valve can simultaneously deliver a dT feed stream from station 4 to the serial linked reaction pots in stages 1 and 4 and a dC feed stream from station 9 to serial linked reaction pots in stages 2 and 5. The other stations can include multi-block valves to allow delivery of different feed stream concentrations to different stages of the synthesis process. For example, it may be desirable to deliver a higher NMI concentration to the capping station in stage 5 than at stage 1. For clarity purposes, it is noted that "stage . . . " includes a schematic representation of a conveyor plate mechanism (see 120 in FIG. 9 below) including "U" shaped inlet/outlet tubing suitable for receiving reaction pots. This conveyor plate mechanism allows reaction pots to be arranged in a suitable array and spacing to most efficiently build the desired biological polymer. The arrays of each stage can be a separate plate wherein reaction pots are removed from a first plate array and attached to the next or the arrays may be mechanically integrated.

Figure 9:
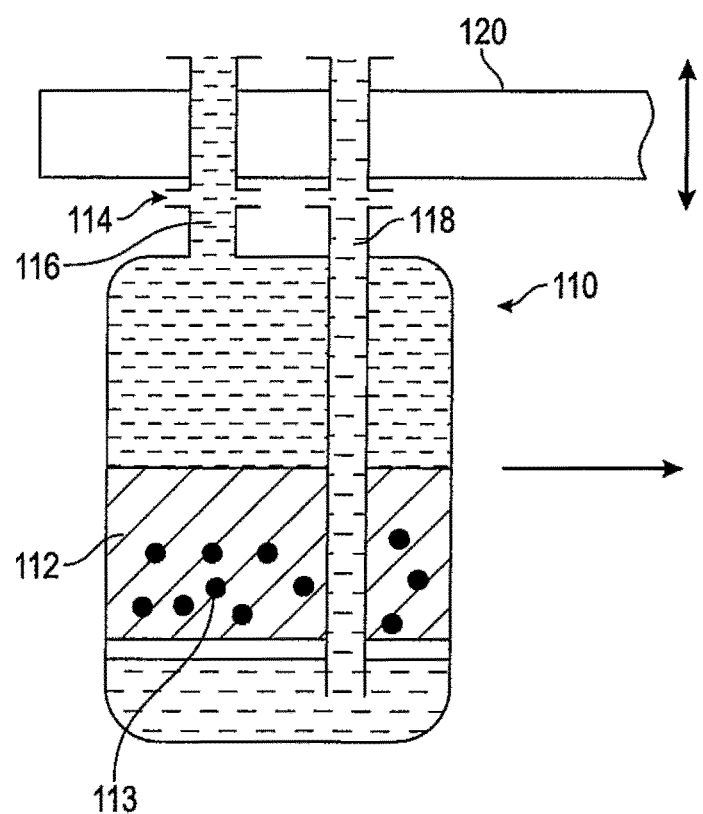
FIG. 9 provides a schematic illustration of a reaction vessel or pot.

FIG. 9 illustrates an exemplary reaction pot 100. Pot 100 can include a vessel 112 including a reaction bed 113. A top surface 114 of the pot can include inlet 116 for introducing the liquid feed stream to a top of the reaction pot and outlet 118 for removing liquid from a lower region of the pot after it has passed through the reaction bed 113. Gas may be introduced through inlet 116 (or another passage) to aid in removal. The reaction pots 100 can be configured to mate with substantially flat plates 120 situated at each station and including sealable mating joints. Plate(s) 120 can move vertically to engage/disengage the reaction pot(s) 110, while the reaction pots 110 move horizontally from station to station. However, it is envisioned that the reaction pot transport mechanism will be able to receive different size and shape pots. The reaction pots can be single use (e.g. a disposable vessel and/or bag) or reused depending on the requirements of the synthesis being performed.

An exemplary reaction pot size may be about 1 to 100 mm, or about 10 to 50 mm inner diameter and up to 150 mm in height. The active dimensions of the support in the reaction pots can be specified. For example, a support in a state swollen by solvent can have a height of about greater than 0 to about 150 mm, or about 5 to 30 mm, or about 10 to 40 mm and a diameter of greater than 0 to about 100 mm or about 10 to 50 mm. It is however noted that vessel shape does not have to be cylindrical.

By operating the system with multiple reaction pots of relatively small volume (e.g. less than 15 cm$^3$) mass transfer is improved for the reaction occurring in each reaction pot. The improved mass transfer can have benefits such as a pressure drop per reaction pot of less than about 5 bars. Nonetheless, when the totality of the system is considered, the use of many reaction pots provides a synthesis apparatus having a reaction volume greater than what is presently practical in a batch process (e.g. 2,000 mm diameter and 200 mm height=3,140 cm$^3$), whereas 200 reaction pots of 40 mm diameter and 150 mm height provides a volume of 9,420 cm$^3$.

The reaction pots may be equipped with a temperature control device, a mixing device, a pressure adjustment apparatus and/or a pH adjusting apparatus. It may be desirable to change the conditions (e.g. temperature) of a reaction pot between stations to maximize the environment for the treatment/reaction being performed. The reaction pot can also include a probe for monitoring at least one of temperature, pressure, pH, conductivity and time.

The reaction pots can also be individually marked (e.g. bar code) for identification. In this manner, aspects of the synthesized molecule of each reaction pot can be stored in a database. This information can include, for example, stage of manufacture, expected or actual molecule structure, date of production, purity, etc.

In certain embodiments, the reaction pots are moved in unison (together but not necessarily to every station) between the stations according to a set period of time (T). However, each step in the synthesis process may not be completed in the same amount of time. Moreover, at least one step may have the longest reaction time (R). Therefore, reaction pots can move position but remain at stations with a reaction time less than R for a multiple of T, which can be a whole number. In this context, at some stations, the reaction pots may be held at the station while the station is inactive.

In a start-up mode, the vessels can be moved after a period of reaction time which is a fraction of T until at least one vessel is associated with each station. After start-up, at least one reaction vessel can be positioned at each station and the normal rate of movement T is commenced. Depending on the molecule being formed, it is envisioned that each reaction pot will move about every few seconds to 10 minutes or about every ½-5 minutes.

Figure 10:
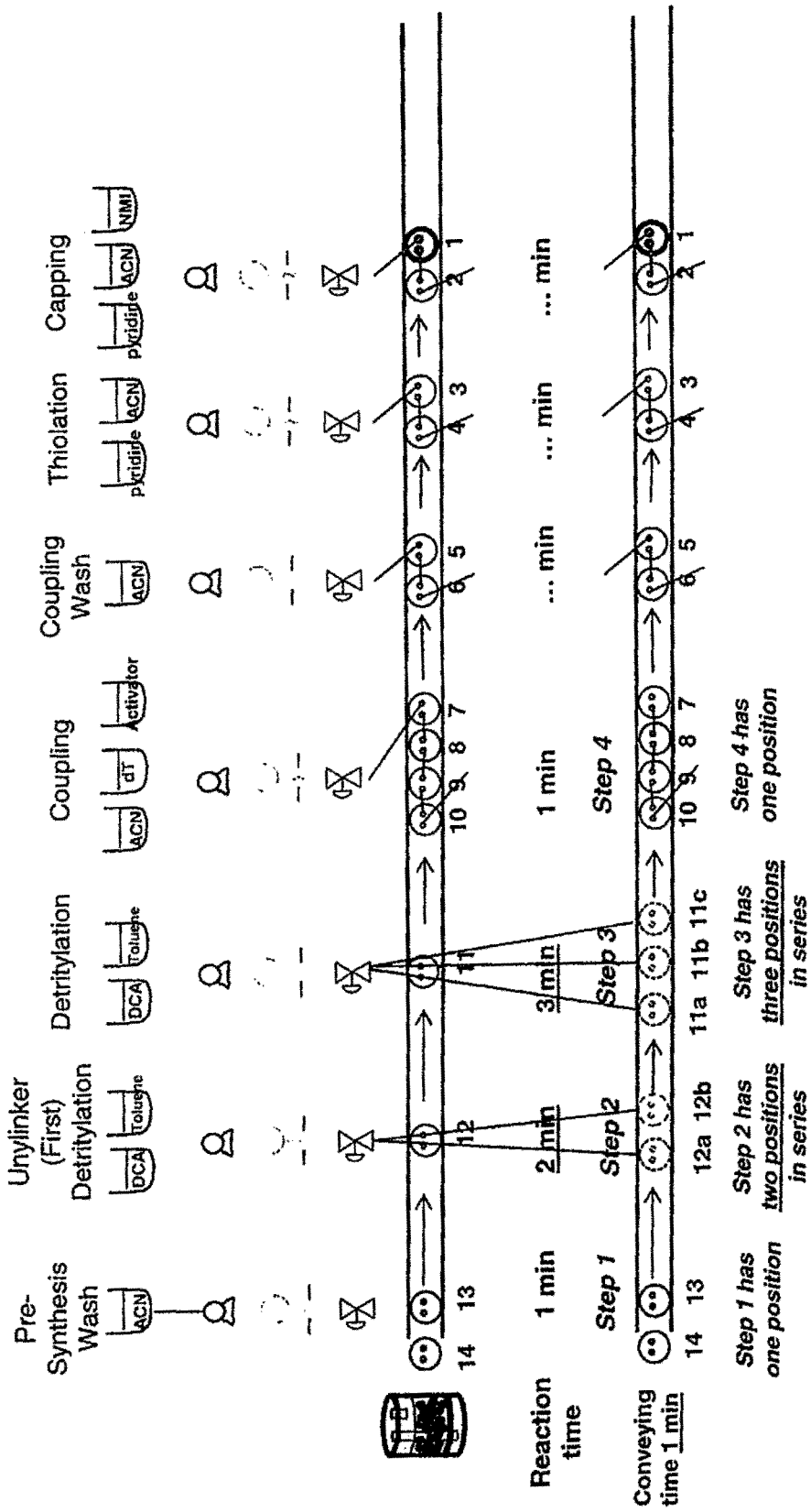
FIG. 10 provides a schematic illustration of how reaction time variances can be addressed using a series protocol.

Referring now to FIG. 10, a concept of operation of the synthesizer of the present disclosure in series according to set time intervals is depicted. Moreover, each step is configured to have pot position equal to the expected reaction time. For example, the detritylation step can have a 3-minute reaction time and a corresponding three pot positions to receive a feed liquid (e.g. DCA/toluene) from a single feed simultaneously. In this configuration, each pot can follow its proceeding pot throughout the assembly.

Figure 11:
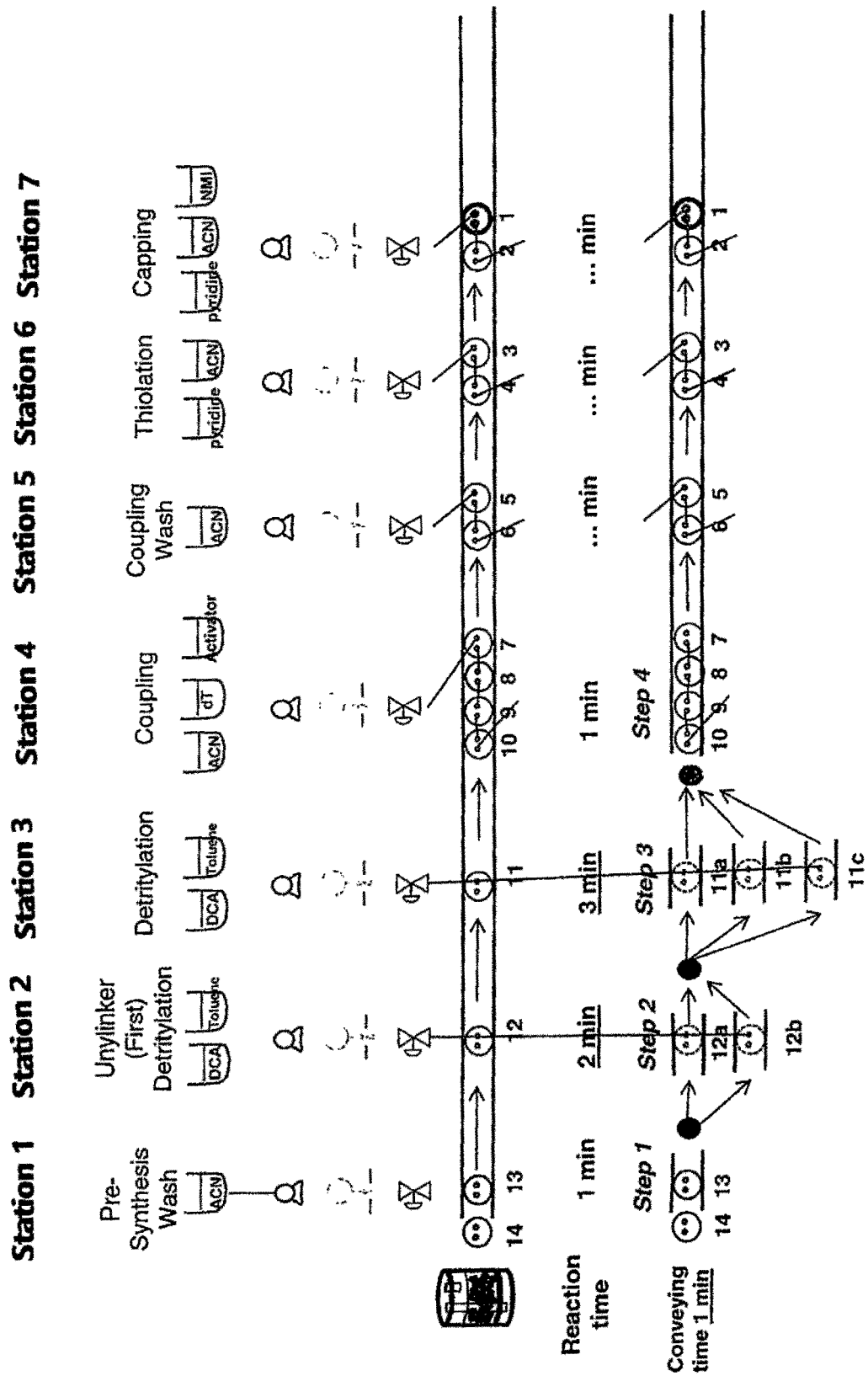
FIG. 11 provides a schematic illustration of how reaction time variances can be addressed using a parallel protocol.

Referring now to FIG. 11, a concept of operating the synthesizer of the present disclosure in parallel according to a set time interval is illustrated. Moreover, the number of pots at a station corresponds to the associated reaction time. For example, two pots are resident at the first detritylation station wherein the DCA/Toluene is fed sequentially from a first of the two pots to a second. In this configuration, pots would move to positions at longer reaction steps which do not follow the immediately preceding pot. In either of the protocols of FIGS. 10 and 11, the intent of the arrangement is to position each pot at the station for a sufficient period of time to complete the reaction. In that context, it is envisioned that the series and/or parallel strategy can be used together and alternatively at the stations.

At the conclusion of the building of the desired macromolecule, the procedure contemplates removal of reaction pots containing the desired macromolecule from the synthesizer apparatus array. Similarly, the procedure contemplates that the stations that have completed feeding to the final reaction pot can stop introducing its designated reagent/reactant. In this context, it is envisioned that each station may include a feed of a cleaning fluid (potentially from a centralized reservoir of cleaning fluid). In this manner, a cycle closing pot could follow the final macromolecule building reaction pot and receive the cleaning fluid used to close each station in the array. An exemplary cleaning fluid is ACN.

It is also contemplated that recycle of reagent/reactant excess from an individual station can be delivered to a different station along the row or even to a station in a different row. This is possible at any point in the building of the macromolecule and when used at the end of a cycle allows a closed reaction station to feed an active reaction station further into the array. For example, rather than recycle the ACN from station 1 back to the station 1 feeding vessel, recycle to station 5 (or other suitable) can be performed to preserve raw materials and improve operational efficiency, particularly at close of a process.

Although specific reagents and reactants are illustrated, the disclosure is not limited to these example(s) or sequence(s). Rather, the skilled artisan will recognize that countless variations in the synthesis sequence are feasible.

The synthesizer can also be configured to dispense reaction solutions that will synthesize polypeptides. The process of peptide synthesis on solid supports generally involves building a peptide from the carboxyl-terminal end. The peptide is attached to a solid support via its carboxy-terminal amino acid and further includes a protecting group on the amino-terminal α-amino group. The protecting group is then cleaved off of the peptide to form a deprotected peptide. Next a monomeric amino-acid, also containing a α-amino protecting group, is contacted with the de-protected peptide under conditions for formation of a peptide bond between the α-amino group of the deprotected peptide and the α-carboxy group the monomeric amino acid. The monomeric amino acid can be provided in an activated form or an activating reagent can be added to the amino acid and growing peptide. Washes can be carried out between steps to remove reagents. The cycle of deprotecting the prior amino acid and coupling the additional amino acid can be repeated until a peptide of the desired length is synthesized. Any reactive side chains of the amino acids are typically protected by chemical groups that can withstand the coupling and α-amino deprotection procedure. These side chain protecting groups, however, can be removed at the end of the synthesis. The array of stations, and the schedule by which the arrays communicate with each other can be correlated in accordance with the teachings herein and the known reaction schemes for peptide synthesis including, for example, those described in Goodman et al. (Eds.) Synthesis of Peptides and Petidomimetics, Vol. E22a. Georg Thieme Verlag, Stuttgart (2002).

The following examples are presented by way of illustration, not limitation.

An oligonucleotide is manufactured using the apparatus described herein according to the physical steps including delivering fluids to multiple reaction pots, and draining fluid from the reaction pots. A computer is programmed to deliver the appropriate reactants to designated reaction pots in a designated sequence.

The oligonucleotide synthesis includes deprotection, condensation, oxidation and capping. Deprotection is removing an acid-labile DMTr group from the 5'-OH of a sugar moiety. Condensation is coupling excess activated monomer to the growing chain. Oxidation is oxidation of 3'-5' internucleotide phosphite triester linkage to a more stable phosphotriester linkage. The polymers are then treated to remove protecting groups, thereby generating the phophodiester linkages. A capping step is capping 5'-hydroxyl groups that failed to condense as acetate esters. The general protocol is 1. washing the support; 2. dispensing a liquid comprising a deblocking agent to remove the protecting group; and draining; 3. dispensing a liquid comprising a protected nucleotide and a coupling activator; draining; 4. dispensing a liquid comprising a capping agent; and draining the liquid; washing the support; and draining the liquid comprising the oxidizer. Steps are repeated until the nucleotide sequence is complete.

Polypeptide synthesis can include the addition of amino acids onto a nascent polypeptide chain by 1. deprotecting (Fmoc or Boc) by removing a group to make an alpha amino group at one end of a growing peptide chain available; 2. Coupling by activating amino acid residue into an active ester and then forming an amide bond with the deprotected alpha-amino group on end of growing peptide chain; and 3. Capping unreacted alpha-amino groups with the same reagent used in DNA/RNA synthesis. In Fmoc synthesis, the base-labile protecting group (Fmoc) is removed at each cycle. At the end of the synthesis, the side chain protecting groups are removed by a weak acid, which also cleaves the bond anchoring the peptide to the support. In Boc chemistry, the Boc protecting group is acid-labile and can be removed with a mild acid. A strong acid is used for the final deprotection and cleavage step.

A protocol for peptide synthesis using Fmoc chemistry can include the following steps: 1. Deprotect (at least once)—piperidine, 2×-7 minutes; 2. Drain; 3. Wash (at least once)-N-methylpyrrolidone (NMP) or dimethylformamide (DMF), 6×; 4. Couple-18 seconds activation+35 minutes coupling 5. Drain; 6. Cap [optional]-1 minute; 7. Drain; 8. Wash (at least once)—NMP or DMF, 3×. Repeat steps 1-8 until amino acid sequence is complete. A protocol for peptide synthesis using Boc chemistry can include the following steps: 1. Wash (at least once)-chloromethane (DCM), 1×; 2. Deprotect (at least once)-trifluoroacetic acid (TFA), 2×-6 minutes; 3. Drain; 4. Wash (at least once)-chloromethane (DCM), 1×; 5. Wash (at least once)-NMP or DMF, 6×; 6. Couple-18 seconds activation+35 minutes coupling; 7. Drain; 8. Cap [optional]-1 minute; 9. Drain; 10. Wash (at least once)-NMP or DMF, 3×. Repeat steps 1-10 until amino acid sequence is complete.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

To aid the Patent Office and any readers of this application and the resulting patent in interpreting the claims appended hereto, applicants do not intend any of the appended claims or claim elements to invoke 35 U.S.C. 112(f) unless the words "means for" or "step for" are explicitly used in the particular claim.

The invention claimed is:

1. A method of nucleic acid synthesis using a device comprising at least one deprotection unit to carry out a step of deprotection, at least one coupling unit to carry out a step of coupling, at least one oxidation/thiolation unit to carry out a step of oxidation or thiolation, and at least one washing unit to carry out a step of washing, wherein, a plurality of reaction vessels for nucleic acid synthesis are moved to the units in accord with a synthesis scheme for a desired nucleic acid sequence, wherein at least two reaction vessels are simultaneously acted upon at several of the units in series such that material introduced from one of the several units into a first of the at least two reaction vessels is subsequently received in a second of the at least two reaction vessels from the first.

2. The method of nucleic acid synthesis according to claim 1, wherein each unit is used only for one type of nucleic acid or processing chemical.

3. The method according to claim 1, wherein at least several of the units are used more than once in the synthesis of the nucleic acid.

4. The method according to claim 1, wherein an amidite is added at greater than a 3:1 stoichiometric requirement during a single addition to a reaction vessel(s).

5. The method according to claim 1, wherein all reaction vessels move simultaneously.

6. The method according to claim 1, wherein at a selected unit, the reaction vessel moves but remains in fluid communication with the same unit.

7. The method according to claim 1, wherein a material used in the coupling unit is phosphoramidite, and the phosphoramidite is added to a single vessel in an amount between from 1.5 to 3.0 equivalents.

8. The method according to claim 1, wherein a material used in the coupling unit is an activator, and the activator is added at different concentrations at different points in the synthesis sequence and wherein a material used in the reaction and washing units is added at different concentrations at different points in the synthesis sequence.

9. The method according to claim 1, wherein a material recovered from a reaction vessel at a unit is reused by the unit for a reaction or treatment of a later reaction vessel in the synthesis scheme.

10. The method according to claim 1, wherein a reaction product in the reaction vessel is evaluated at several or all reaction stations and wherein a reaction vessel demonstrating an unsatisfactory result is removed from the synthesis procedure.

11. The method of claim 1 wherein, a plurality of reaction vessels are moved to the units via a conveyor device in accord with a synthesis scheme for building a selected nucleic acid sequence; wherein at least one unit performs a reaction requiring a longest time (R) relative to the other units; wherein the stations are operated in parallel; and wherein at least a majority said vessels are moved in unison between the units according to a set period of time (T), said vessels remaining at units with a reaction time less than R for a multiple of T.

12. The method according to claim 11 including a start-up mode wherein the vessels are moved after a period of reaction time which is a fraction of T until at least one vessel is associated with each station and wherein after the start-up mode, multiple vessels are serially linked at one or more station(s) and the vessels move at a time equal to or approaching T.

13. An apparatus for the multi-stage synthesis of organic molecules, said apparatus comprising in combination: (a) a plurality of reaction vessels; (b) a plurality of fluid reservoirs; (c) valve elements associated with said fluid reservoirs; (d) fluid delivery devices for providing a feed stream from the fluid reservoirs to said vessels; (e) a plurality of devices capable of monitoring a chemical composition of effluent from a plurality of said vessels; and (f) a conveyor having a programmed pattern suitable for transporting the vessels from fluid engagement with one fluid reservoir to a subsequent fluid reservoir sequentially according to the programmed pattern, wherein at least two reaction vessels receive a fluid from at least one of the fluid reservoirs simultaneously and wherein the fluid from the at least one of the fluid reservoirs is introduced into a first reaction vessel and from the first reaction vessel into a second reaction vessel of the at least two reaction vessels.

14. The apparatus according to claim 13 wherein each fluid reservoir comprises a reaction and/or treatment station and, wherein at least one station is simultaneously connected with at least two vessels in series.

15. The apparatus according to claim 14, wherein the fluid reservoirs are connected with the reaction vessels as counter-current or co-current flow mechanisms.

16. The apparatus according to claim 13, wherein each vessel is temperature controlled, includes a mixing device, or is capable of adjustable pressure and/or pH.

17. The apparatus according to claim 13 being comprised of at least 100 reaction vessels.

18. The apparatus according to claim 13, wherein if a monitoring device identifies an effluent outside of a predetermined range, the associated vessel can be removed from the programmed pattern.

19. The apparatus according to claim 13, comprising at least X fluid reservoirs and at least Y vessels, wherein Y>X.

* * * * *